United States Patent [19]

DiNinno et al.

[11] Patent Number: 5,220,011

[45] Date of Patent: * Jun. 15, 1993

[54] INTERMEDIATES FOR PREPARING 2-HETEROARYLPHENYL-CARBAPENEM ANTIBACTERIAL AGENTS

[75] Inventors: Frank P. DiNinno, Old Bridge; Ravindra N. Guthikonda, Edison; Susan M. Schmitt, Scotch Plains, all of N.J.

[73] Assignee: Merck & Co., Inc., Rahway, N.J.

[*] Notice: The portion of the term of this patent subsequent to Sep. 1, 2009 has been disclaimed.

[21] Appl. No.: 720,324

[22] Filed: Jun. 25, 1991

[51] Int. Cl.$^5$ .................................. C07D 477/00
[52] U.S. Cl. ............................................ 540/302
[58] Field of Search ................................ 540/302

[56] References Cited

U.S. PATENT DOCUMENTS

| | | | |
|---|---|---|---|
| 4,260,627 | 4/1981 | Christensen et al. | 424/274 |
| 4,465,632 | 8/1984 | Christensen et al. | 260/245.2 |
| 4,543,257 | 9/1985 | Cama et al. | 514/210 |
| 4,775,669 | 10/1988 | Cama et al. | 514/240 |
| 4,978,659 | 12/1990 | DiNinno et al. | 514/210 |
| 5,004,739 | 4/1991 | Salzmann et al. | 514/210 |
| 5,004,740 | 4/1991 | Salzmann et al. | 514/210 |
| 5,006,519 | 4/1991 | DiNinno et al. | 514/210 |
| 5,011,832 | 4/1991 | Salzmann et al. | 514/210 |
| 5,025,006 | 6/1991 | Salzmann et al. | 514/210 |
| 5,025,007 | 6/1991 | Greenlee et al. | 514/210 |
| 5,025,008 | 6/1991 | DiNinno et al. | 514/210 |
| 5,032,587 | 7/1991 | DiNinno et al. | 514/210 |
| 5,034,384 | 7/1991 | Greenlee et al. | 514/210 |
| 5,034,385 | 7/1991 | DiNinno et al. | 514/210 |
| 5,037,820 | 8/1991 | DiNinno et al. | 514/210 |

FOREIGN PATENT DOCUMENTS 0277743 8/1988 European Pat. Off. .

OTHER PUBLICATIONS

L. D. Cama et al., Total Synthesis of Thienamycin Analogs-III Tetrahedron 39, 2531 (1983).
R. N. Guthikonda et al., Structure Activity Relationship in the 2-Arylcarbapenem Series, J. Med. Chem., 30, 871 (1987).
Ser. No. 650,111, Feb. 1991 T. Rano et al.
Ser. No. 596,145, Oct. 1990, M. L. Greenlee et al.

*Primary Examiner*—Robert Gerstl
*Attorney, Agent, or Firm*—Gabriel Lopez; Joseph F. DiPrima

[57] ABSTRACT

Carbapenem intermediates of the formula

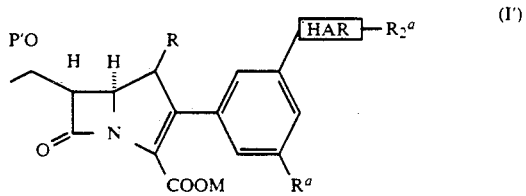

(I')

where:
M is a removable protecting group for carboxy, and
P' is a removable protecting group for hydroxy
are useful intermediates for preparing antibacterial agents.

10 Claims, No Drawings

INTERMEDIATES FOR PREPARING 2-HETEROARYLPHENYL-CARBAPENEM ANTIBACTERIAL AGENTS

BACKGROUND OF THE INVENTION

The present invention relates to antibacterial agents of the carbapenem class, in which the 2-position side-chain is characterized by a heteroarylphenyl moiety, substituted by various substituents, as described in more detail below.

Thienamycin was an early carbapenem antibacterial agent having a broad spectrum; it has the following formula:

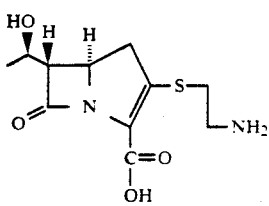

Later, N-formimidoyl thienamycin was discovered; it has the formula:

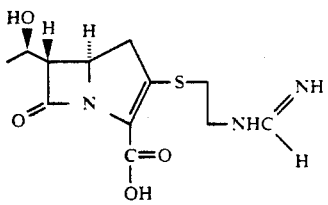

The 2-heteroarylphenyl-carbapenems of the present invention are not characterized by a broad antibacterial spectrum such as that of thienamycin or N-formimidoyl thienamycin. Rather, their spectrum of activity is largely limited to gram positive microorganisms, especially methicillin resistant *Staphylococcus aureus* (MRSA), methicillin resistant *Staphylococcus epidermidis* (MRSE), and methicillin resistant coagulase negative Staphylococci (MRCNS). The antibacterial compounds of the present invention thus comprise an important contribution to therapy of these difficult to control pathogens. Moreover, there is an increasing need for agents effective against such pathogens (MRSA/MRCNS) which are at the same time safe, i.e., free from undesirable toxic side effects. No β-lactam antibacterial has yet been found which meets these requirements. And, the current agent of choice, vancomycin, a glycopeptide antibacterial, is experiencing an ever increasing amount od resistance in the MRSA/MRCNS pathogens.

More recently, carbapenem antibacterial agents have been described which have a 2-substituent which is an aryl moiety optional substituted by, e.g., aminomethyl and substituted aminomethyl. These agents are described in U.S. Pat. Nos. 4,543,257 and 4,260,627 and have the formula:

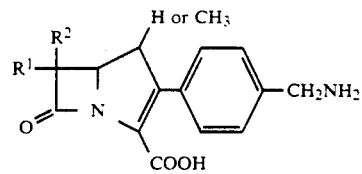

However, there is no description or suggestion of a heteroarylphenyl 2-substituent such as characterizes the compounds of the present invention, nor is there any suggestion of the surprisingly better anti-MRSA/MRCNS activity of the compounds of the present invention.

U.S. Pat. No. 4,978,659 described a particular class of compounds of the formula:

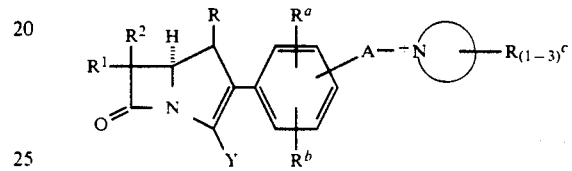

but this limited teaching in no way suggests the totally different compounds of the present invention, nor their surprisingly better anti-MRSA/MRCNS activity.

SUMMARY OF INVENTION

The present invention provides novel carbapenem compounds of the formula:

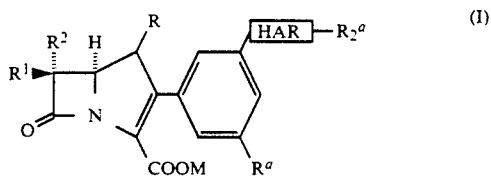

(I)

wherein:

R is H or CH$_3$;

R$^1$ and R$^2$ are independently H, CH$_3$—, CH$_3$CH$_2$—, (CH$_3$)$_2$CH—, HOCH$_2$—, CH$_3$CH(OH)—, (CH$_3$)$_2$C(OH)—, FCH$_2$CH(OH)—, F$_2$CHCH(OH)—, F$_3$CCH(OH)—, CH$_3$CH(F)—, CH$_3$CF$_2$—, or (CH$_3$)$_2$C(F)—;

[HAR]

is a 5- or 9-membered mono- or bicyclic heteroaryl ring system wherein 1 atom is O or S, or an 8-membered bicyclic heteroaryl ring system wherein 2 atoms are O and/or S;

R$^a$ is each independently selected from the group consisting of hydrogen and the radicals set out below:

a) a trifluoromethyl group: —CF$_3$;

b) a halogen atom: —Br, —Cl, —F, or —I;

c) C$_1$-C$_4$ alkoxy radical: —OC$_{1-4}$ alkyl, wherein the alkyl is optionally mono-substituted by R$^q$, where R$^q$ is a member selected from the group consisting of —OH, —OCH$_3$, —CN, —C(O)NH$_2$, —OC(O)NH$_2$, CHO, —OC(O)N(CH$_3$)$_2$, —SO$_2$NH$_2$, —SO$_2$N(CH$_3$)$_2$, —SOCH$_3$, —SO$_2$CH$_3$, —F, —CF$_3$, —COOM$^a$ (where M$^a$ is hydrogen, alkali metal, methyl or phenyl), tetrazolyl (where the point of attachment is the carbon atom of the tetrazole ring and one of the nitrogen atoms is mono-substituted by $M^a$ as defined above) and —$SO_3M^b$ (where $M^b$ is hydrogen or an alkali metal);

d) a hydroxy group: —OH;

e) a carbonyloxy radical: —O(C=O)$R^s$, where $R^s$ is $C_1$-$C_4$ alkyl or phenyl, each of which is optionally mono-substituted by $R^q$ as defined above or tri-substituted with —F;

f) a carbamoyloxy radical: —O(C=O)N($R^y$)$R^z$, where $R^y$ and $R^z$ are independently H, $C_{1-4}$ alkyl (optionally mono-substituted by $R^q$ as defined above), together a 3- to 5-membered alkylidene radical to form a ring (optionally substituted with $R^q$ as defined above) or together a 2- to 4-membered alkylidene radical, interrupted by —O—, —S—, —S(O)—, —S(O)$_2$— or —N$R^e$—, to form a ring (where $R^e$ is hydrogen, $C_1$-$C_4$ alkyl, and $C_1$-$C_4$ alkyl mono-substituted with $R^q$ and the ring is optionally mono-substituted with Rq as defined above);

g) a sulfur radical: —S(O)$_n$—$R^s$ where n=0-2, and $R^s$ is defined above;

h) a sulfamoyl group: —SO$_2$N($R^y$)$R^z$ where $R^y$ and $R^z$ are as defined above;

i) azido: $N_3$ j) a formamido group: —N($R^t$)—C(O)H, where $R^t$ is H or $C_1$-$C_4$ alkyl, and the alkyl thereof is optionally mono-substituted by $R^q$ as defined above;

k) a ($C_1$-$C_4$ alkyl)carbonylamino radical: —N($R^t$)—C(O)$C_1$-$C_4$ alkyl, where $R^t$ is as defined above, and the alkyl group is also optionally mono-substituted by $R^q$ as defined above;

l) a ($C_1$-$C_4$ alkoxy)carbonylamino radical: —N($R^t$)—C(O)O$C_1$-$C_4$ alkyl, where $R^t$ is as defined above, and the alkyl group is also optionally mono-substituted by $R^q$ as defined above;

m) a ureido group: —N($R^t$)—C(O)N($R^y$)$R^z$ where $R^t$, $R^y$ and $R^z$ are as defined above;

n) a sulfonamide group: —N($R^t$)SO$_2R^s$, where $R^s$ and $R^t$ are as defined above;

o) a cyano group: —CN;

p) a formyl or acetalized formyl radical: —C(O)H or —C(OCH$_3$)$_2$H;

q) ($C_1$-$C_4$ alkyl)carbonyl radical wherein the carbonyl is acetalized: —C(OCH$_3$)$_2C_1$-$C_4$ alkyl, where the alkyl is optionally mono-substituted by $R^q$ as defined above;

r) carbonyl radical: —C(O)$R^s$, where $R^s$ is defined above;

s) a hydroximinomethyl radical in which the oxygen or carbon atom is optionally substituted by a $C_1$-$C_4$ alkyl group: —C($R^y$)=NO$R^z$ where $R^y$ and $R^z$ are as defined above, except they may not be joined together to form a ring;

t) a ($C_1$-$C_4$ alkoxy)carbonyl radical: —C(O)O$C_{1-4}$ alkyl, where the alkyl is optionally mono-substituted by $R^q$ as defined above;

u) a carbamoyl radical: —C(O)N($R^y$)$R^z$ where $R^y$ and $R^z$ are as defined above;

v) an N-hydroxycarbamoyl or N($C_1$-$C_4$ alkoxy)carbamoyl radical in which the nitrogen atom may be additionally substituted by a $C_1$-$C_4$ alkyl group: —(C=O)—N(O$R^y$)$R^z$ where $R^y$ and $R^z$ are as defined above, except they may not be joined together to form a ring;

w) a thiocarbamoyl group: —C(S)N($R^y$)($R^z$) where $R^y$ and $R^z$ are as defined above;

x) carboxyl: —COO$M^b$, where $M^b$ is as defined above;

y) thiocyanate: —SCN;

z) trifluoromethylthio: —SCF$_3$;

aa) tetrazolyl, where the point of attachment is the carbon atom of the tetrazole ring and one of the nitrogen atoms is mono-substituted by hydrogen, an alkali metal or a $C_1$-$C_4$ alkyl optionally substituted by $R^q$ as defined above;

ab) an anionic function selected from the group consisting of: phosphono [P=O(O$M^b$)$_2$]; alkylphosphono {P=O(O$M^b$)—[O($C_1$-$C_4$ alkyl)]}; alkylphosphinyl [P=O(O$M^b$)—($C_1$-$C_4$ alkyl)]; phosphoramido [P=O(O$M^b$)N($R^y$)$R^z$ and P=O(O$M^b$)NH$R^x$]; sulfino (SO$_2M^b$); sulfo (SO$_3M^b$); acylsulfonamides selected from the structures CON$M^b$SO$_2R^x$, CON$M^b$SO$_2$N($R^y$)$R^z$, SO$_2$N$M^b$CON($R^y$)$R^z$; and SO$_2$N$M^b$CN, where $R^x$ is phenyl or heteroaryl, where heteroaryl is a monocyclic aromatic hydrocarbon group having 5 or 6 ring atoms, in which a carbon atom is the point of attachment, in which one of the carbon atoms has been replaced by a nitrogen atom, in which one additional carbon atom is optionally replaced by a heteroatom selected from O or S in the case of a 5-membered ring, and in which from 1 to 2 additional carbon atoms are optionally replaced by a nitrogen heteroatom, and where the phenyl and heteroaryl are optionally mono-substituted by $R^q$, as defined above; $M^b$ is as defined above; and $R^y$ and $R^z$ are as defined above;

ac) $C_5$-$C_7$ cycloalkyl group in which one of the carbon atoms in the ring is replaced by a heteroatom selected from O, S, NH or N($C_1$-$C_4$ alkyl) and in which one additional carbon atom may be replaced by NH or N($C_1$-$C_4$ alkyl), and in which at least one carbon atom adjacent to each nitrogen heteroatom has both of its attached hydrogen atoms replaced by one oxygen thus forming a carbonyl moiety and there are one or two carbonyl moieties present in the ring;

ad) $C_2$-$C_4$ alkenyl radical, optionally mono-substituted by one of the substituents a) to ac) above and phenyl which is optionally substituted by $R^q$ as defined above;

ae) $C_2$-$C_4$ alkynyl radical, optionally mono-substituted by one of the substituents a) to ac) above;

af) $C_1$-$C_4$ alkyl radical;

ag) $C_1$-$C_4$ alkyl mono-substituted by one of the substituents a)-ac) above;

ah) a 2-oxazolidinonyl moiety in which the point of attachment is the nitrogen atom of the oxazolidinone ring, the ring oxygen atom is optionally replaced by a heteroatom selected from —S— and N$R^t$ (where $R^t$ is as defined above) and one of the saturated carbon atoms of the oxazolidinone ring is optionally mono-substituted by one of the substituents a) to ag) above; and M is selected from:

i) hydrogen;

ii) a pharmaceutically acceptable esterifying group or removable carboxyl protecting group; or iii) an alkali metal or other pharmaceutically acceptable cation.

The present invention also provides novel carbapenem intermediates of the formula:

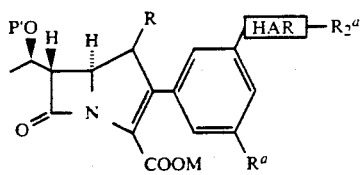

(I')

wherein:

R is H or $CH_3$;

$R^q$ is defined above, with the proviso that $R^q$ additionally includes OP' where P' is defined below, that $M^a$ and $M^b$ of $R^q$ both include M and that the Type d) hydroxy substituent additionally may be protected hydroxy, OP';

P' is a removable protecting group for hydroxy; and

M is a removable protecting group for carboxy.

Preferred intermediates have the formula:

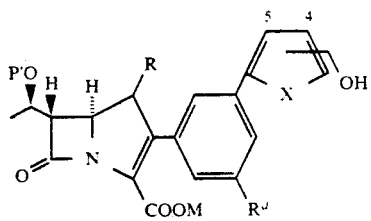

wherein:

R is H or $CH_3$;

P' is a removable protecting group for hydroxy;

M is a removable protecting group for carboxy;

$R^a$ is selected from the group consisting of H, OP', Cl, Br, I, $SCH_3$, CN, CHO, $SOCH_3$, $SO_2CH_3$, $CO_2M$, $CH_2OP'$ or $CONH_2$; and with the proviso that the —$CH_2OH$ substituent is in the 3- or 4-position of the heteroaromatic ring; and X is O or S.

DETAILED DESCRIPTION OF THE INVENTION

The manufacture of compounds of Formula I may be carried out in a three-stage synthetic scheme followed by deprotection. The objective of the first synthetic stage is to produce a base heteroarylphenyl (hereinafter HAP) compound which may be converted to be the two-position substituent of the carbapenem of Formula I. The objective of the second synthetic stage is to attach the base HAP to the carbapenem. Finally, the objective of the third synthetic stage is to substitute the HAP with the desired $R^a$. This third synthetic stage may either be performed after the first synthetic stage or after the second synthetic stage according to the nature of the desired $R^a$.

Flow Sheet A demonstrates a suggested first stage synthesis. Flow Sheets B1 and B2 demonstrate a second stage synthesis. The third stage synthesis varies according to the selected $R^a$.

FLOW SHEET A

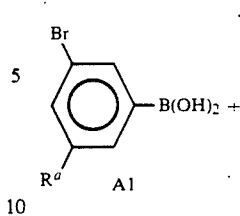

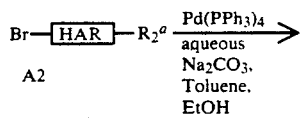

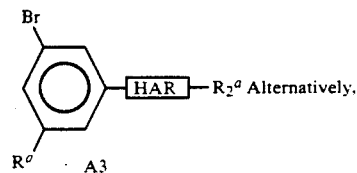

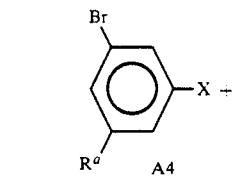

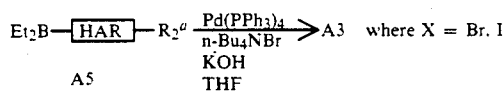

Flow Sheet A

Substituted bromophenylboronic acids A1 and substituted heteroaryldiethylboranes A5 may be prepared by conventional methods. Exposure of either of these boron compounds to aryl halides in the presence of a catalytic amount of palladium catalyst yields the desired synthons A3.

Some of these desired synthons A3 may be prepared by the general synthetic routes published in the literature.

Flow Sheet B1

The second stage synthesis is to attach the base HAP to the 2-position of the carbapenem. With compatible $R^a$ or suitable precursor substituents therefor, HAP A3 may be added to azetidin-2-one B1 in a Grignard reaction as shown in Flow Sheet B. (B1 is subgeneric to the more general B1*. Replacing B1 by B1* (where M is as defined above under ii) produces a broader class of compounds analogous to B2, B3, and B4.)

The Grignard reaction requires that A3 be converted to a Grignard reagent by reaction with magnesium and 1,2-dibromoethane in THF from 20° C. to 60° C. and subsequently contacting A3 as a Grignard reagent with B1 in THF at from −70° C. to about 20° C. to produce azetidin-2-one B2. Alternatively, A3 may be reacted with t-butyllithium, n-butyllithium, or the like in $Et_2O$ or THF at from −78° to −50° C. followed by the addition of magnesium bromide to produce the same Grignard reagent. $R^i$ of B1 is in practice pyridin-2-yl but may clearly be a variety of substituents including aromatic and heteroaromatic substituents. Further, $R^i$ might be, for example, phenyl, pyrimidinyl or thiazolyl.

Azetidin-2-one B2 is an intermediate that may be ring closed to a carbapenem. It is on this intermediate that $R^a$ or precursor substituent such as t-butyldimethylsilyloxy-methyl group should be modified where such methyl, may be accomplished. Removal of the protecting groups then provides the final compound Formula I. Such final elaboration and deprotection is described in further detail below.

FLOW SHEET B1

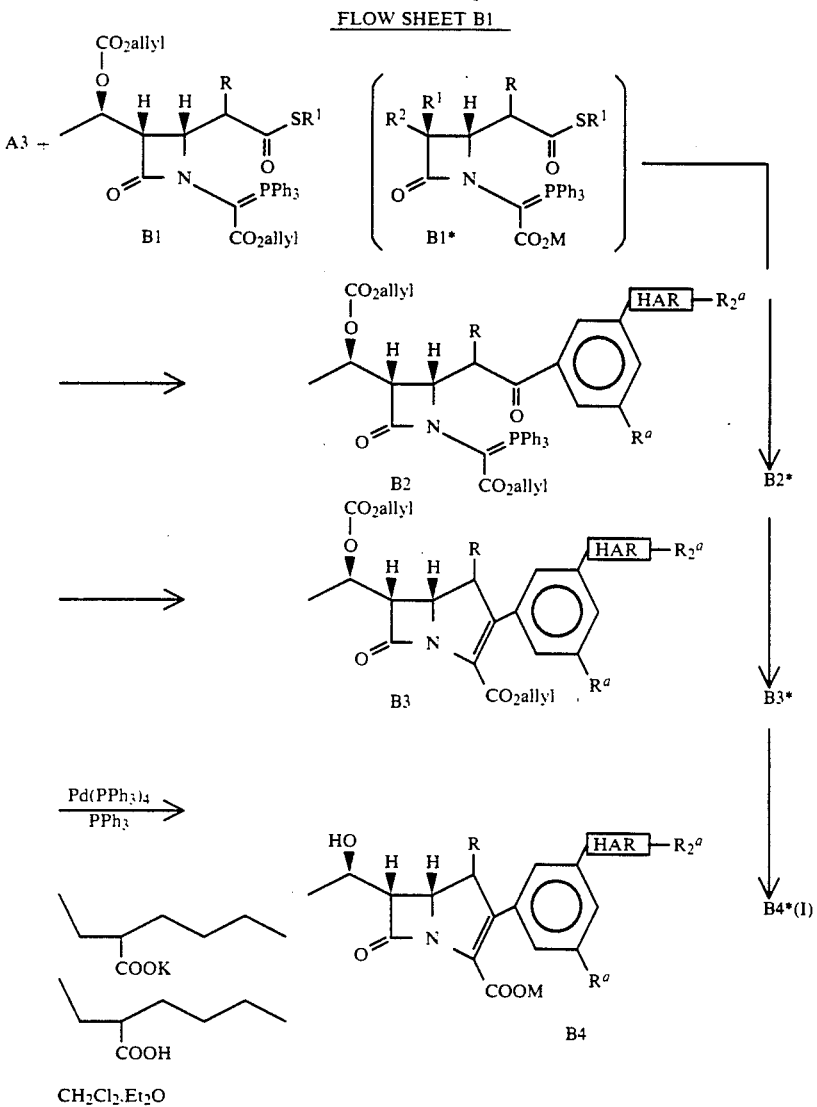

modification is incompatible with the carbapenem nucleus. For example, a convenient reaction to remove the t-butyldimethylsilyl group from a hydroxymethyl substituent of the HAP on compound B2 is to expose compound B2 to a dilute solution of sulfuric acid or hydrochloric acid in methanol at 0° C. If the t-butyldimethylsilyl group were removed from carbapenem B3 under the same conditions, a substantial portion of carbapenem would be degraded and lost. Thus, modification of the precursor substituent in this instance and replacement with another precursor substituent or even $R^a$ is best performed before closing the carbapenem. Of course it is possible to remove the t-butyldimethylsilyl group from carbapenem B3 in reduced yield by exposing B3 to tetra-n-butylammonium fluoride and acetic acid in THF.

Compound B2 may be ring closed to carbapenem B3 by refluxing in xylene with p-hydroquinone for about 1 to 2 hours. It is on this intermediate that final elaboration of $R^a$ from a precursor substituent, e.g. hydroxy- Flow Sheet B2

Flow Sheet B2 shows an alternative second stage synthesis, i.e. attachment of the base HAP such as B5 to the 2-position of the carbapenem. This synthesis involves a palladium catalyzed cross-coupling reaction between a carbapenem triflate and a suitably substituted arylstannane, a process which is described in U.S. Ser. No. 650,111 filed Feb. 4, 1991. In order to apply this synthesis, it is first necessary to modify B5 to the trimethylstannylheteroarylphenyl B6. This is accomplished by reacting B5 with t-butyllithium in THF at from −78° to −50° C. followed by the addition of trimethyltin chloride. Alternatively, B6 may be prepared by simply heating B5 with hexamethylditin in the presence of tetrakistriphenylphosphine palladium in toluene solution. At this intermediate stage, it may be desirable to remove certain protecting groups if employed on a precursor substituent $R^a$. For instance, a protecting group such as t-butyldimethylsilyl on a hydroxymethyl substituent may be removed by exposure to tetra-n-butylammonium fluoride in THF yielding a particular B6. If the t-butyldimethylsilyl group were removed from carbapenem B7 under the same conditions, a substantial portion of the carbapenem would be degraded and lost. Thus, modification of the precursor substituent in this instance and replacement with another precursor substituent or even an $R^a$ is best performed before attachment to the carbapenem.

The steps for preparing the 2-oxocarbapenam intermediate B8 are well known in the art and are explained in ample detail by D. G. Melillo et al., *Tetrahedron Letters*, 21, 2783 (1980), T. Salzmann et al., *J. Am. Chem. Soc.*, 102, 6161 (1980), and L. M. Fuentes, I. Shinkai, and T. N. Salzmann, *J. Am. Chem. Soc.*, 108, 4675 (1986). The syntheses are also discussed in U.S. Pat. Nos. 4,269,772; 4,350,631; 4,383,946; and 4,414,155 all incorporated herein by reference.

Referring again to Flow Sheet B2, the 2-oxocarbapenam, B8, is reacted at $-78°$ C. to $-50°$ C. with a suitable trifluoromethanesulfonyl source, such as trifluoromethanesulfonic anhydride, trifluoromethanesulfonyl chloride and the like, in the presence of an organic nitrogen base, such as triethylamine, diisopropylamine and the like, in a polar aprotic solvent, such as tetrahydrofuran or methylene chloride. Optionally, an organic nitrogen base, such as triethylamine and the like, is then added to the reaction solution followed immediately by a silylating agent, such as trimethylsilyl trifluoromethanesulfonate to provide intermediate B9. An aprotic polar coordinating solvent, such as DMF, 1-methyl-2-pyrrolidinone and the like, is optionally added. This is followed by the addition of a palladium compound, such as tris(dibenzylideneacetone)dipalladium-chloroform ($Pd_2(DBA)_3$•$CHCl_3$), palladium acetate and the like, optionally, a suitably substituted phenylphosphine, such as tris(4-methoxyphenyl)phosphine, tris(2,4,6-trimethoxy phenyl)phosphine and the like, and the stannane B6. A halide source such as lithium chloride, zinc chloride or ammonium chloride and the like, is added and the reaction solution is allowed to warm and is stirred at a suitable temperature, such as 0° to 50° C. for from a few minutes to 48 hours. The carbapenem B7 is obtained by conventional isolation/purification methodology known in the art.

Generally speaking, the milder conditions of the synthesis shown in Flow Sheet B2 allow for a wider range of functional group $R^a$ to be present than the synthesis illustrated in Flow Sheet B1. However, in certain cases, it is advantageous for the $R^a$ substituent(s) of the stannane B6 to be introduced in a protected or precursory form. Final elaboration of $R^a$ from a precursor substituent, e.g. hydroxymethyl, may be accomplished on carbapenem intermediate B7. Removal of hydroxyl and ester protecting groups then provides the final compound, C5 of Formula I. Such final elaboration and deprotection is described in detail below.

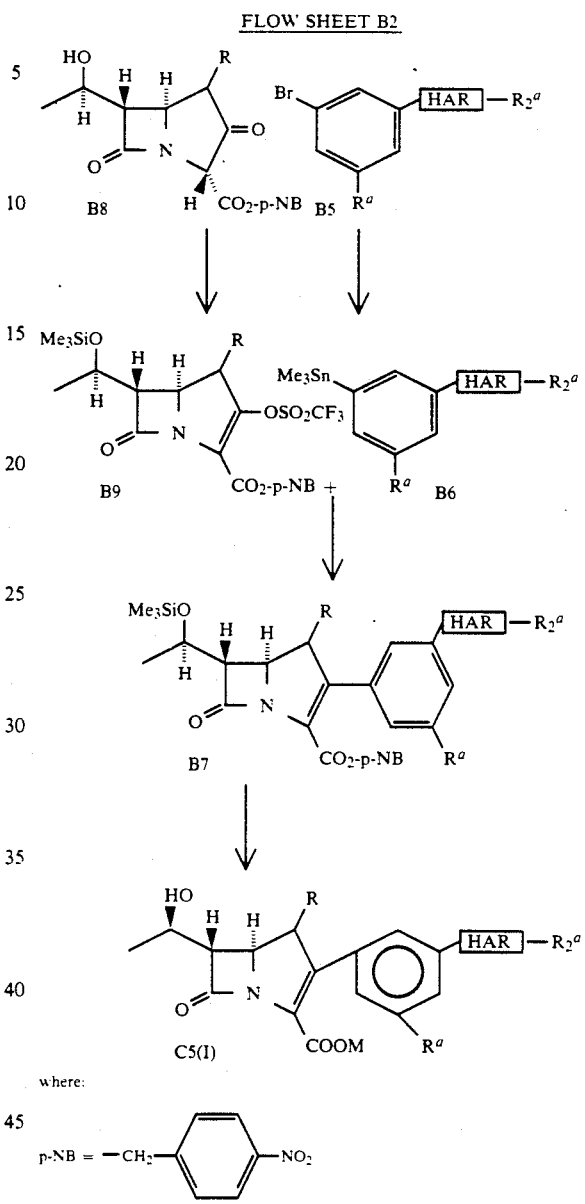

Flow Sheet C

Azetidin-2-ones B1 and B1* (Flow Sheet B1), pyridyl-thioesters, are well known compounds in the production of carbapenems. Diverse synthetic schemes useful to make B1 and B1* may be imagined by the skilled artisan. Particularly useful to the instant inventors is a synthetic scheme set out further in Flow Sheet C below in which the symbol R is as defined above. The steps for preparing intermediate B1 and B1* are analogous to the procedures described, for example, in U.S. Pat. Nos. 4,260,627 and 4,543,257; L. D. Cama et al. *Tetrahedron* 39, 2531 (1983); R. N. Guthikonda et al. *J. Med. Chem.*, 30, 871 (1987) hereby incorporated by reference, as discussed below.

FLOW SHEET C

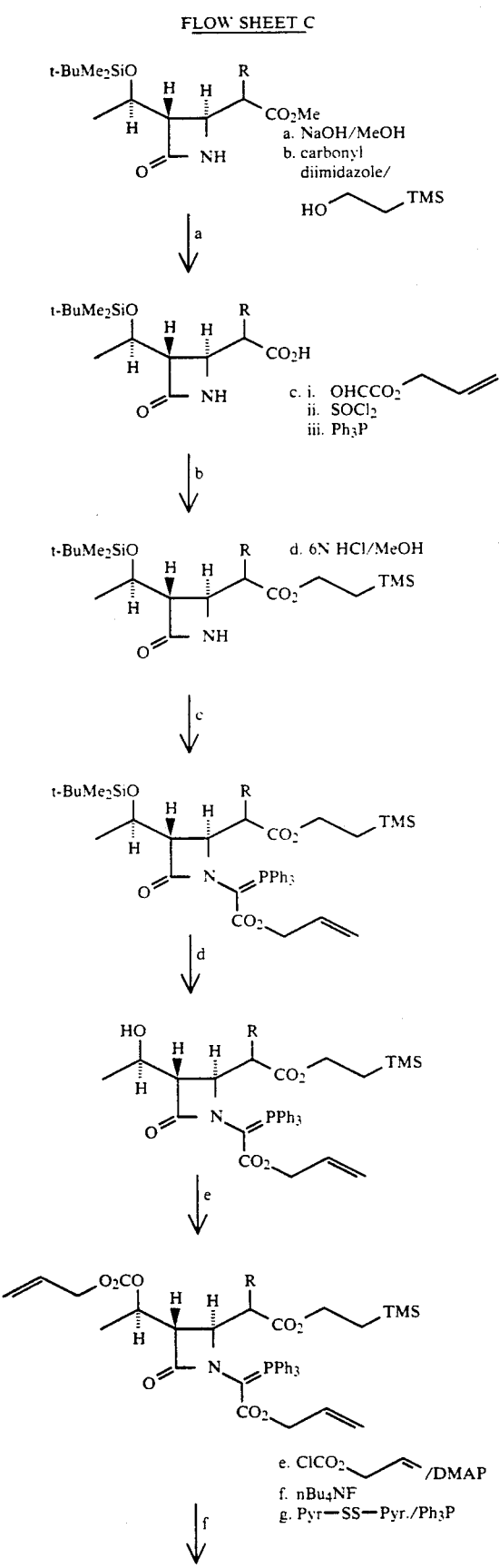

e. ClCO₂⟶/DMAP
f. nBu₄NF
g. Pyr—SS—Pyr./Ph₃P

-continued
FLOW SHEET C

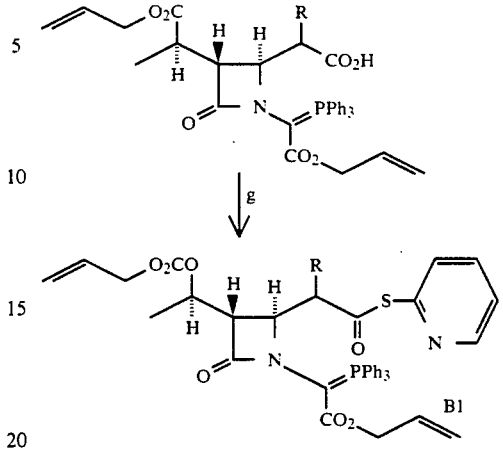

The general synthesis description depicted above in the Flow Sheets shows a protected 1-hydroxyethyl substitution on the 6-position of the carbapenem. After final deprotection, a 1-hydroxyethyl substituent is obtained, which is preferred in most cases. However, it has been found that with certain 2-side-chain selections, the ultimate balance of favorable properties in the overall molecule may be enhanced by selection of the 6-(1-fluoroethyl) moiety instead. Preparation of 6-fluoroalkyl compounds within the scope of the present invention is carried out in a straightforward manner using techniques well known in the art of preparing carbapenem antibacterial compounds. See, e.g., J. G. deVries et al., *Heterocycles*, 23(8), 1915 (1985); BE 900 718 A (Sandoz) and Japanese Patent Pub. No. 6-0163-882-A (Sanruku Ocean).

In the compounds of the present invention, the $R^a$ substituents can be selected based on the biological properties which they confer. In related compounds, it has been found that the neutral or anionic substituted compounds afford greater water solubility and reduced potential for CNS side effects. Substituents which tend to confer improved water solubility on the overall compound have been found useful, since they are contemplated to thereby improve the transport of the compound involved. Although a substantial number and range of substituents have been described herein, all of these are contemplated to be a part of the present invention based on the biological performance of substituents related in terms of their medicinal chemistry.

|HAR| is a 5-, 8-, or 9-membered mono- or bicyclic aromatic ring system wherein up to two carbon atoms are replaced by O or S. HAR can be represented by

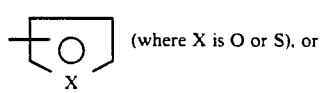 (where X is O or S), or

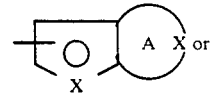 or

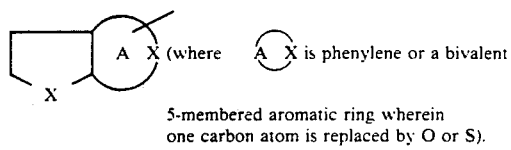

(where [A X] is phenylene or a bivalent 5-membered aromatic ring wherein one carbon atom is replaced by O or S).

Thus, this aryl structure may be the radical of a 5-membered furan or thiophene, of an 8-membered furofuran, thienofuran, or thienothiophene, or of a 9-membered benzofuran or benzothiophene. The carbon atom at the point of attachment, however, cannot be replaced by a heteroatom.

The $R^a$ substituents are on the carbon atoms of the aryl ring system but not on the one at the point of attachment. It is preferred that $R^a = H$ when it is α to the point of attachment.

In preferred compounds of Formula I, $R^1$ is hydrogen. More preferably, $R^1$ is hydrogen and $R^2$ is (R)—$CH_3CH(OH)$— or (R)—$CH_3CH(F)$—. In the most preferred case, $R^1$ is H and $R^2$ is (R)—$CH_3CH(OH)$. While R=H is usually preferred, there are instances in which R=$CH_3$ may provide improved chemical stability, water solubility, or pharmacokinetic behavior. The substituent R=$CH_3$ may be of either configuration, i.e., the α or β-stereoisomer. Additionally, in preferred compounds, at least one $R^a$ in the meta-position of the HAP moiety from the point of attachment to the other aromatic ring is other than hydrogen. In the most preferred compounds, in total, up to two $R^a$ substituents are other than hydrogen.

Among preferred $R^a$ substituents are $C_1$-$C_4$ alkyl mono-substituted with hydroxy, such as, hydroxymethyl; formyl; carbamoyl, such as, —$CONH_2$; hydroxyiminomethyl, such as, —CH=NOH; cyano; or halogen such as chloro, bromo, and iodo.

Flow Sheet D

In regard to this preferred substitution, the hydroxymethyl group may be obtained in the $R^a$ position of the phenyl portion of HAP as shown in Flow Sheet D, in which A3 is obtained as given in Flow Sheet A. Selective metallation of A3 and formylation with N,N-dimethylformamide provides synthon D1. Reduction of D1 with sodium borohydride in methanol yields the preferred substituent which is protected as its silylether in the next step to give D3. The latter reagent is then incorporated into Flow Sheet B1 as A3. The preferred hydroxymethyl group may also be obtained in the appropriate $R^a$ positions of the heteroaryl portion of HAP. Thus, by a judicious choice of starting materials as exhibited in Flow Sheet A, the desired substitution pattern is readily available.

FLOW SHEET D

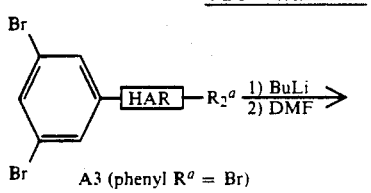

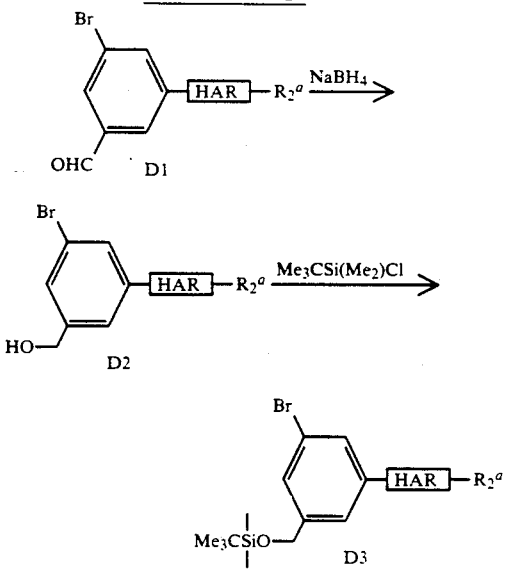

The preferred formyl substitution on the HAP moiety may be obtained from the hydroxymethyl substitution of B3 or isomeric B3* described in Flow Sheet B1 by a Swern oxidation. For example, isomeric B3 is oxidized in methylene chloride at from −70° C. to room temperature employing oxalyl chloride-dimethyl sulfoxide as the active agent. Obviously, the position of the resultant formyl substitution will depend upon the position of the hydroxymethyl substitution in isomeric B3.

The preferred —CH=NOH substitution on the HAP moiety may be conveniently obtained from the formyl substitution just described. This is accomplished simply by exposing the formyl substituted compound to hydroxylamine in an appropriate solvent at room temperature.

The preferred cyano substitution on the HAP moiety may be obtained from the —CH=NOH substitution just described. The —CH=NOH substituted compound is dehydrated with triflic anhydride and triethylamine in a solvent at −70° C.

The preferred carbamoyl substitution, —$CONH_2$, may be obtained from B2 or "isomeric" B2 by oxidizing hydroxymethyl with Jones reagent to the corresponding carboxylic acid substitution as described above. This carboxylic acid is converted to —$CONH_2$ by sequentially contacting with 1-ethyl-3-(3-dimethyl-aminopropyl)carbodiimide hydrochloride, 1-hydroxy-benzotriazole, and ammonia in an organic solvent at room temperature. Substituted amides may of course be obtained by replacing ammonia with the corresponding substituted amine. In contrast to the carboxylic acid substitution, this carbamoyl substituent requires no protection from the conditions of carbapenem cyclization. Deprotection following cyclization is carried out with palladium catalyzed deallylation in a solution containing potassium or sodium 2-ethylhexanoate as described in McCombie and Jeffrey, *J. Org. Chem.*, 47, 2505 (1983). Deprotection in such a solution yields the desired potassium or sodium salt.

In the preparation methods described above, the carboxyl group at the 3-position and the hydroxyl group at the 8-position of the carbapenem remain blocked by protecting groups until the final product is prepared. Suitable hydroxyl protecting groups, P', are silyl groups such as trialkylsilyl, aryl(alkyl)alkoxysilyl, alkoxydiarylsilyl and diarylalkylsilyl and carbonate groups such as alkyloxycarbonyl, substituted alkyloxycarbonyl, benzyloxycarbonyl, substituted benzyloxycarbonyl, allyloxycarbonyl and substituted allyloxycarbonyl. The preferred protecting groups, in addition to or including those shown in the schemes, are t-butylmethoxyphenylsilyl, t-butoxydiphenylsilyl, trimethylsilyl, triethylsilyl, t-butyldimethylsilyl, o-nitrobenzyloxycarbonyl, p-nitrobenzyloxycarbonyl, benzyloxycarbonyl, t-butyloxycarbonyl, 2,2,2-trichloroethyloxycarbonyl and allyloxycarbonyl. Suitable carboxyl protecting groups, M, in addition to or including those shown in the schemes are described herein below.

Deblocking may be carried out in a conventional manner, with care being taken to avoid a procedure which is so harsh as to disrupt other portions of the final product molecule. For compounds prepared according to Flow Sheet B1, deprotection may be carried out in a palladium catalyzed reaction in a solution containing potassium 2-ethylhexanoate and 2-ethylhexanoic acid or, alternatively, another suitable nucleophile such as pyrrolidine. Alternatively, for those prepared via Flow Sheet B2, deprotection is conducted sequentially. Thus, compound B7 is exposed initially to aqueous acidic conditions, acetic acid or dilute HCl or the like, in an organic solvent such as tetrahydrofuran at 0° C. to ambient temperature for from a few minutes to several hours. The resulting desilylated carbapenem may be isolated by conventional techniques, but is more conveniently taken into the final deprotection process. Thus, addition of an inorganic base such as NaHCO$_3$ or KHCO$_3$ and a catalyst, such as, 10% Pd/C or 5% Rh/Al$_2$O$_3$ followed by hydrogenation provides for the removal of the p-nitrobenzyl protecting group and the formation of the final compound of Formula I.

With reference to the above definitions, "alkyl" means a straight or branched chain aliphatic hydrocarbon radical.

The term "heteroatom" means N, S, or O, selected on an independent basis.

The term "heteroaryl" has been defined herein, in relation to the $R^x$ group, to have a specific and limited meaning, being only monocyclic. It is required that the monocyclic heteroaryl have at least one nitrogen atom, and optionally at most only one additional oxygen or sulfur heteroatom may be present. Heteroaryls of this type are pyrrole and pyridine (1N); and oxazole, thiazole or oxazine (1N+1O or 1S). While additional nitrogen atoms may be present together with the first nitrogen and oxygen or sulfur, giving, e.g., a thiadiazole (2N's+1S), the preferred heteroaryls are those where only nitrogen heteroatoms are present when there is more than one. Typical of these are pyrazole, imidazole, pyrimidine and pyrazine (2N's) and triazine (3N's).

The heteroaryl group of $R^x$ is always optionally mono-substituted by $R^q$, defined above, and substitution can be on one of the carbon atoms or one of the heteroatoms, although in the latter case certain substituent choices may not be appropriate.

Listed in Table I are specific compounds of the instant invention. In the table, $R^2$ substituents containing a chiral center (i.e., —CH(F)CH$_3$ and —CH(OH)CH$_3$) have the (R) configuration, and the $R^a$ column refers to the substituent on the phenyl ring.

TABLE I

I'

[Structure: carbapenem core with R, R$^2$, HAR—R$_2^a$, COOM, R$^a$ substituents]

| No. | R | R$^2$ | M | R$^a$ | HAR-R$_2^a$ |
|-----|---|-------|---|-------|-------------|
| 1 | H | —CH(OH)CH$_3$ | Na | H | thiophene |
| 2 | H | —CH(OH)CH$_3$ | K | H | furan |
| 3 | H | —CH(OH)CH$_3$ | Na | Cl | thiophene |
| 4 | H | —CH(OH)CH$_3$ | Na | Cl | furan |
| 5 | H | —CH(OH)CH$_3$ | Na | Br | thiophene |

TABLE I-continued
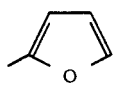
| No. | R | $R^2$ | M | $R^a$ | HAR-$R_2^a$ |
|---|---|---|---|---|---|
| 6 | H | —CH(OH)CH$_3$ | Na | Br | 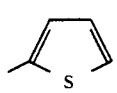 |
| 7 | H | —CH(OH)CH$_3$ | Na | I | 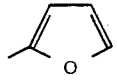 |
| 8 | H | —CH(OH)CH$_3$ | Na | I | 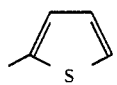 |
| 9 | H | —CH(OH)CH$_3$ | Na | SMe | 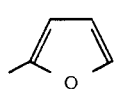 |
| 10 | H | —CH(OH)CH$_3$ | Na | SMe | 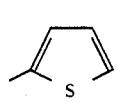 |
| 11 | H | —CH(OH)CH$_3$ | Na | S(O)Me | 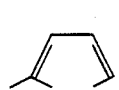 |
| 12 | H | —CH(OH)CH$_3$ | Na | S(O)Me | 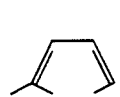 |
| 13 | H | —CH(OH)CH$_3$ | Na | SO$_2$Me | 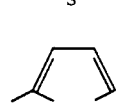 |
| 14 | H | —CH(OH)CH$_3$ | Na | SO$_2$Me | 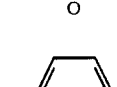 |
| 15 | H | —CH(OH)CH$_3$ | Na | F | 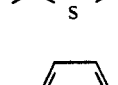 |
| 16 | H | —CH(OH)CH$_3$ | Na | F | 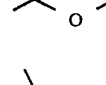 |
| 17 | H | —CH(OH)CH$_3$ | K | H | 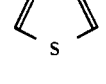 |
| 18 | H | —CH(OH)CH$_3$ | Na | H | |

TABLE I-continued
| No. | R | R² | M | Rᵃ | HAR-R₂ᵃ |
|---|---|---|---|---|---|
| 19 | H | —CH(OH)CH₃ | Na | F |  |
| 20 | H | —CH(OH)CH₃ | Na | F |  |
| 21 | H | —CH(OH)CH₃ | Na | Cl |  |
| 22 | H | —CH(OH)CH₃ | Na | Cl |  |
| 23 | H | —CH(OH)CH₃ | Na | Br |  |
| 24 | H | —CH(OH)CH₃ | Na | Br |  |
| 25 | H | —CH(OH)CH₃ | Na | I |  |
| 26 | H | —CH(OH)CH₃ | Na | I |  |
| 27 | H | —CH(OH)CH₃ | Na | CH₂OH |  |
| 28 | H | —CH(OH)CH₃ | Na | CH₂OH |  |
| 29 | H | —CH(OH)CH₃ | Na | CHO |  |
| 30 | H | —CH(OH)CH₃ | Na | CHO | |

TABLE I-continued

Structure I':

Core structure with substituents R, R², HAR-R₂ᵃ, COOM, Rᵃ on a β-lactam fused ring attached to phenyl with HAR-R₂ᵃ group.

| No. | R | R² | M | Rᵃ | HAR-R₂ᵃ |
|-----|---|-----|----|------|---------|
| 31 | H | —CH(OH)CH₃ | Na | CH=NOH | 5-methyl-thiophene |
| 32 | H | —CH(OH)CH₃ | Na | CH=NOH | 5-methyl-furan |
| 33 | H | —CH(OH)CH₃ | Na | CN | 5-methyl-thiophene |
| 34 | H | —CH(OH)CH₃ | Na | CN | 5-methyl-furan |
| 35 | H | —CH(OH)CH₃ | K | H | 5-methyl-thiophene-2-CH₂OH |
| 36 | H | —CH(OH)CH₃ | K | H | 5-methyl-furan-2-CH₂OH |
| 37 | H | —CH(OH)CH₃ | Na | H | 5-methyl-thiophene-2-CHO |
| 38 | H | —CH(OH)CH₃ | Na | H | 5-methyl-furan-2-CHO |
| 39 | H | —CH(OH)CH₃ | Na | H | 5-methyl-thiophene-2-CH=NOH |
| 40 | H | —CH(OH)CH₃ | Na | H | 5-methyl-furan-2-CH=NOH |
| 41 | H | —CH(OH)CH₃ | Na | H | 5-methyl-thiophene-2-CN |
| 42 | H | —CH(OH)CH₃ | Na | H | 5-methyl-furan-2-CN |
| 43 | H | —CH(OH)CH₃ | Na | F | 5-methyl-thiophene-2-CH₂OH |

TABLE I-continued

| No. | R | R² | M | Rᵃ | HAR-R₂ᵃ |
|---|---|---|---|---|---|
| 44 | H | —CH(OH)CH₃ | Na | F | 5-methyl-furan-2-yl-CH₂OH |
| 45 | H | —CH(OH)CH₃ | Na | F | 5-methyl-thiophen-2-yl-CHO |
| 46 | H | —CH(OH)CH₃ | Na | F | 5-methyl-furan-2-yl-CHO |
| 47 | H | —CH(OH)CH₃ | Na | F | 5-methyl-furan-2-yl-COOH |
| 48 | H | —CH(OH)CH₃ | Na | F | 5-methyl-thiophen-2-yl-CH=NOH |
| 49 | H | —CH(OH)CH₃ | Na | F | 5-methyl-furan-2-yl-CH=NOH |
| 50 | H | —CH(OH)CH₃ | Na | F | 5-methyl-thiophen-2-yl-CN |
| 51 | H | —CH(OH)CH₃ | Na | F | 5-methyl-furan-2-yl-CN |
| 52 | H | —CH(OH)CH₃ | Na | Cl | 5-methyl-thiophen-2-yl-CH₂OH |
| 53 | H | —CH(OH)CH₃ | Na | Cl | 5-methyl-furan-2-yl-CH₂OH |
| 54 | H | —CH(OH)CH₃ | Na | Cl | 5-methyl-thiophen-2-yl-CHO |
| 55 | H | —CH(OH)CH₃ | Na | Cl | 5-methyl-furan-2-yl-CHO |
| 56 | H | —CH(OH)CH₃ | Na | Cl | 5-methyl-thiophen-2-yl-CH=NOH |

TABLE I-continued

| No. | R | R² | M | Rᵃ | HAR-R₂ᵃ |
|---|---|---|---|---|---|
| 57 | H | —CH(OH)CH₃ | Na | Cl | 5-methyl-furan-2-yl-CH=NOH |
| 58 | H | —CH(OH)CH₃ | Na | Cl | 5-methyl-thiophen-2-yl-CN |
| 59 | H | —CH(OH)CH₃ | Na | Cl | 5-methyl-furan-2-yl-CN |
| 60 | H | —CH(OH)CH₃ | Na | Br | 5-methyl-thiophen-2-yl-CH₂OH |
| 61 | H | —CH(OH)CH₃ | Na | Br | 5-methyl-furan-2-yl-CH₂OH |
| 62 | H | —CH(OH)CH₃ | Na | Br | 5-methyl-thiophen-2-yl-CHO |
| 63 | H | —CH(OH)CH₃ | Na | Br | 5-methyl-furan-2-yl-OH |
| 64 | H | —CH(OH)CH₃ | Na | Br | 5-methyl-thiophen-2-yl-CH=NOH |
| 65 | H | —CH(OH)CH₃ | Na | Br | 5-methyl-furan-2-yl-CH=NOH |
| 66 | H | —CH(OH)CH₃ | Na | Br | 5-methyl-thiophen-2-yl-CN |
| 67 | H | —CH(OH)CH₃ | Na | Br | 5-methyl-furan-2-yl-CN |
| 68 | H | —CH(OH)CH₃ | Na | I | 5-methyl-thiophen-2-yl-OH |
| 69 | H | —CH(OH)CH₃ | Na | I | 5-methyl-furan-2-yl-OH |

TABLE I-continued

| No. | R | $R^2$ | M | $R^a$ | HAR-$R_2^a$ |
|---|---|---|---|---|---|
| 70 | H | —CH(OH)CH$_3$ | Na | I | 5-methyl-thiophene-2-CHO |
| 71 | H | —CH(OH)CH$_3$ | Na | I | 5-methyl-furan-2-CHO |
| 72 | H | —CH(OH)CH$_3$ | Na | I | 5-methyl-thiophene-2-CH=NOH |
| 73 | H | —CH(OH)CH$_3$ | Na | I | 5-methyl-furan-2-CH=NOH |
| 74 | H | —CH(OH)CH$_3$ | Na | I | 5-methyl-thiophene-2-CN |
| 75 | H | —CH(OH)CH$_3$ | Na | I | 5-methyl-furan-2-CN |
| 76 | H | —CH(OH)CH$_3$ | Na | CH$_2$OH | 5-methyl-thiophene-2-CH$_2$OH |
| 77 | H | —CH(OH)CH$_3$ | Na | CH$_2$OH | 5-methyl-furan-2-CH$_2$OH |
| 78 | H | —CH(OH)CH$_3$ | Na | CHO | 5-methyl-thiophene-2-CHO |
| 79 | H | —CH(OH)CH$_3$ | Na | CHO | 5-methyl-furan-2-CHO |
| 80 | H | —CH(OH)CH$_3$ | Na | CHO | 5-methyl-thiophene-3-CH$_2$OH |
| 81 | H | —CH(OH)CH$_3$ | Na | CHO | 5-methyl-furan-3-CH$_2$OH |
| 82 | H | —CH(OH)CH$_3$ | Na | H | 5-methyl-thiophene-3-CHO |

TABLE I-continued

| No. | R | R² | M | Rᵃ | HAR-R₂ᵃ |
|-----|---|-----|-----|-----|---------|
| 83 | H | —CH(OH)CH₃ | Na | H | 5-methyl-furan-3-CHO |
| 84 | H | —CH(OH)CH₃ | Na | H | 5-methyl-thiophene-3-CH=NOH |
| 85 | H | —CH(OH)CH₃ | Na | H | 5-methyl-furan-3-CH=NOH |
| 86 | H | —CH(OH)CH₃ | Na | H | 5-methyl-thiophene-3-CN |
| 87 | H | —CH(OH)CH₃ | Na | H | 5-methyl-furan-3-CN |
| 88 | H | —CH(OH)CH₃ | Na | F | 5-methyl-thiophene-3-CH₂OH |
| 89 | H | —CH(OH)CH₃ | Na | F | 5-methyl-furan-3-CH₂OH |
| 90 | H | —CH(OH)CH₃ | Na | F | 5-methyl-thiophene-3-CHO |
| 91 | H | —CH(OH)CH₃ | Na | F | 5-methyl-furan-3-CHO |
| 92 | H | —CH(OH)CH₃ | Na | F | 5-methyl-thiophene-3-CH=NOH |
| 93 | H | —CH(OH)CH₃ | Na | F | 5-methyl-furan-3-CH=NOH |

TABLE I-continued
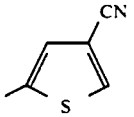
| No. | R | R² | M | Rᵃ | HAR-R₂ᵃ |
|---|---|---|---|---|---|
| 94 | H | —CH(OH)CH₃ | Na | F | 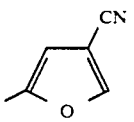 |
| 95 | H | —CH(OH)CH₃ | Na | F | 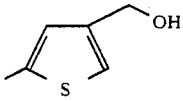 |
| 96 | H | —CH(OH)CH₃ | Na | Cl | 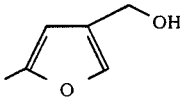 |
| 97 | H | —CH(OH)CH₃ | Na | Cl | 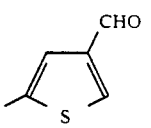 |
| 98 | H | —CH(OH)CH₃ | Na | Cl | 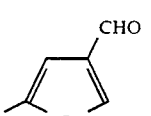 |
| 99 | H | —CH(OH)CH₃ | Na | Cl | 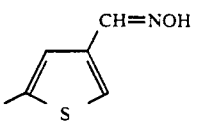 |
| 100 | H | —CH(OH)CH₃ | Na | Cl | 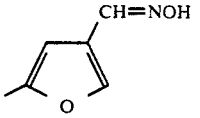 |
| 101 | H | —CH(OH)CH₃ | Na | Cl | 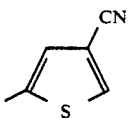 |
| 102 | H | —CH(OH)CH₃ | Na | Cl | 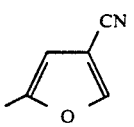 |
| 103 | H | —CH(OH)CH₃ | Na | Cl | 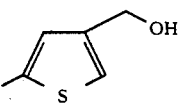 |
| 104 | H | —CH(OH)CH₃ | Na | Br | |

TABLE I-continued

| No. | R | R² | M | Rᵃ | HAR-R₂ᵃ |
|---|---|---|---|---|---|
| 105 | H | —CH(OH)CH₃ | Na | Br | 5-methyl-furan-3-yl-CH₂OH |
| 106 | H | —CH(OH)CH₃ | Na | Br | 5-methyl-thiophen-3-yl-CHO |
| 107 | H | —CH(OH)CH₃ | Na | Br | 5-methyl-furan-3-yl-CHO |
| 108 | H | —CH(OH)CH₃ | Na | Br | 5-methyl-thiophen-3-yl-CH=NOH |
| 109 | H | —CH(OH)CH₃ | Na | Br | 5-methyl-furan-3-yl-CH=NOH |
| 110 | H | —CH(OH)CH₃ | Na | Br | 5-methyl-thiophen-3-yl-CN |
| 111 | H | —CH(OH)CH₃ | Na | Br | 5-methyl-furan-3-yl-CN |
| 112 | H | —CH(OH)CH₃ | Na | I | 5-methyl-thiophen-3-yl-CH₂OH |
| 113 | H | —CH(OH)CH₃ | Na | I | 5-methyl-furan-3-yl-CH₂OH |
| 114 | H | —CH(OH)CH₃ | Na | I | 5-methyl-thiophen-3-yl-CHO |
| 115 | H | —CH(OH)CH₃ | Na | I | 5-methyl-furan-3-yl-CHO |

TABLE I-continued

| No. | R | R² | M | Rᵃ | HAR-R₂ᵃ |
|-----|---|-----|----|----|---------|
| 116 | H | —CH(OH)CH₃ | Na | I | 5-methylthiophene-3-CH=NOH |
| 117 | H | —CH(OH)CH₃ | Na | I | 5-methylfuran-3-CH=NOH |
| 118 | H | —CH(OH)CH₃ | Na | I | 5-methylthiophene-3-CN |
| 119 | H | —CH(OH)CH₃ | Na | I | 5-methylfuran-3-CN |
| 120 | H | —CH(OH)CH₃ | Na | H | 5-methylthiophene-2-SCH₃ |
| 121 | H | —CH(OH)CH₃ | Na | H | 5-methylfuran-2-SCH₃ |
| 122 | H | —CH(OH)CH₃ | Na | H | 5-methylthiophene-2-S(O)CH₃ |
| 123 | H | —CH(OH)CH₃ | Na | H | 5-methylfuran-2-S(O)CH₃ |
| 124 | H | —CH(OH)CH₃ | Na | H | 5-methylthiophene-2-SO₂CH₃ |
| 125 | H | —CH(OH)CH₃ | Na | H | 5-methylfuran-2-SO₂CH₃ |
| 126 | H | —CH(OH)CH₃ | Na | F | 5-methylthiophene-2-SCH₃ |

TABLE I-continued

| No. | R | R² | M | Rᵃ | HAR-R₂ᵃ |
|---|---|---|---|---|---|
| 127 | H | —CH(OH)CH₃ | Na | F | 5-methyl-furan-2-yl-SCH₃ |
| 128 | H | —CH(OH)CH₃ | Na | F | 5-methyl-thiophen-2-yl-S(→O)CH₃ |
| 129 | H | —CH(OH)CH₃ | Na | F | 5-methyl-furan-2-yl-S(→O)CH₃ |
| 130 | H | —CH(OH)CH₃ | Na | F | 5-methyl-thiophen-2-yl-SO₂CH₃ |
| 131 | H | —CH(OH)CH₃ | Na | F | 5-methyl-furan-2-yl-SO₂CH₃ |
| 132 | H | —CH(OH)CH₃ | Na | Cl | 5-methyl-thiophen-2-yl-SCH₃ |
| 133 | H | —CH(OH)CH₃ | Na | Cl | 5-methyl-furan-2-yl-SCH₃ |
| 134 | H | —CH(OH)CH₃ | Na | Cl | 5-methyl-thiophen-2-yl-S(→O)CH₃ |
| 135 | H | —CH(OH)CH₃ | Na | Cl | 5-methyl-furan-2-yl-S(→O)CH₃ |
| 136 | H | —CH(OH)CH₃ | Na | Cl | 5-methyl-thiophen-2-yl-SO₂CH₃ |
| 137 | H | —CH(OH)CH₃ | Na | Cl | 5-methyl-furan-2-yl-SO₂CH₃ |

TABLE I-continued

| No. | R | R² | M | Rᵃ | HAR-R₂ᵃ |
|---|---|---|---|---|---|
| 138 | H | —CH(OH)CH₃ | Na | Br | 5-methylthiophen-2-yl-SCH₃ |
| 139 | H | —CH(OH)CH₃ | Na | Br | 5-methylfuran-2-yl-SCH₃ |
| 140 | H | —CH(OH)CH₃ | Na | Br | 5-methylthiophen-2-yl-S(O)CH₃ |
| 141 | H | —CH(OH)CH₃ | Na | Br | 5-methylfuran-2-yl-S(O)CH₃ |
| 142 | H | —CH(OH)CH₃ | Na | Br | 5-methylthiophen-2-yl-SO₂CH₃ |
| 143 | H | —CH(OH)CH₃ | Na | Br | 5-methylfuran-2-yl-SO₂CH₃ |
| 144 | H | —CH(OH)CH₃ | Na | I | 5-methylthiophen-2-yl-SCH₃ |
| 145 | H | —CH(OH)CH₃ | Na | I | 5-methylfuran-2-yl-SCH₃ |
| 146 | H | —CH(OH)CH₃ | Na | I | 5-methylthiophen-2-yl-S(O)CH₃ |
| 147 | H | —CH(OH)CH₃ | Na | I | 5-methylfuran-2-yl-S(O)CH₃ |
| 148 | H | —CH(OH)CH₃ | Na | I | 5-methylthiophen-2-yl-SO₂CH₃ |

TABLE I-continued

| No. | R | R² | M | Rᵃ | HAR-R₂ᵃ |
|---|---|---|---|---|---|
| 149 | H | —CH(OH)CH₃ | Na | I | 5-methyl-2-(methylsulfonyl)furan |
| 150 | CH₃ | —CH(OH)CH₃ | Na | H | 2-methylthiophene |
| 151 | CH₃ | —CH(OH)CH₃ | Na | H | 2-methylfuran |
| 152 | CH₃ | —CH(OH)CH₃ | Na | H | 3-methylthiophene |
| 153 | CH₃ | —CH(OH)CH₃ | Na | H | 3-methylfuran |
| 154 | CH₃ | —CH(OH)CH₃ | Na | H | 4-methyl-2-formylthiophene |
| 155 | H | —CH(OH)CH₃ | Na | H | 4-methyl-2-formylfuran |
| 156 | H | —CH(OH)CH₃ | Na | H | 5-methyl-3-formylthiophene |
| 157 | H | —CH(OH)CH₃ | Na | H | 5-methyl-3-formylfuran |
| 158 | H | —CH(OH)CH₃ | Na | Br | 2-methylthiophene |
| 159 | H | —CH(OH)CH₃ | Na | Br | 2-methylfuran |
| 160 | H | —CH(OH)CH₃ | Na | Br | 3-methylthiophene |

TABLE I-continued

| No. | R | R² | M | Rᵃ | HAR-R₂ᵃ |
|---|---|---|---|---|---|
| 161 | CH₃ | —CH(OH)CH₃ | Na | Br | 3-methylfuran |
| 162 | H | —CH(F)CH₃ | Na | H | 2-methylthiophene |
| 163 | H | —CH(F)CH₃ | Na | H | 2-methylfuran |
| 164 | H | —CH(OH)CH₃ | Na | H | 2-methylbenzothiophene |
| 165 | H | —CH(OH)CH₃ | Na | H | 2-methylbenzofuran |
| 166 | H | —CH(OH)CH₃ | Na | H | 3-methylbenzothiophene |
| 167 | H | —CH(OH)CH₃ | Na | H | 3-methylbenzofuran |
| 168 | H | —CH(OH)CH₃ | Na | H | methyl-thienothiophene |
| 169 | H | —CH(OH)CH₃ | Na | H | methyl-furofuran |
| 170 | H | —CH(OH)CH₃ | Na | CN | 3-methylthiophene |
| 171 | H | —CH(OH)CH₃ | Na | H | methyl-thienothiophene |

TABLE I-continued
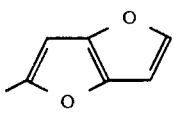
| No. | R | R² | M | Rᵃ | HAR-R₂ᵃ |
|---|---|---|---|---|---|
| 172 | H | —CH(OH)CH₃ | Na | H | 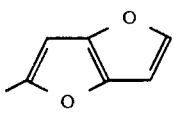 |
| 173 | H | —CH(OH)CH₃ | Na | H | 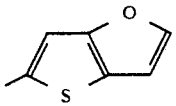 |
| 174 | H | —CH(OH)CH₃ | Na | H | 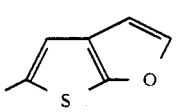 |
| 175 | H | —CH(OH)CH₃ | Na | H | 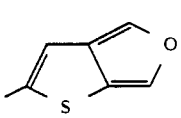 |
| 176 | H | —CH(OH)CH₃ | Na | H | 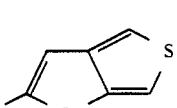 |
| 177 | H | —CH(OH)CH₃ | Na | CN | 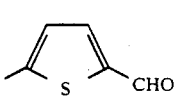 |
| 178 | H | —CH(OH)CH₃ | Na | CN | 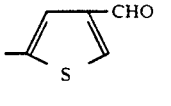 |
| 179 | H | —CH(OH)CH₃ | Na | CN | 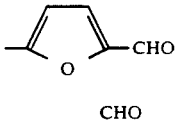 |
| 180 | H | —CH(OH)CH₃ | Na | CN | 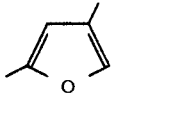 |
| 181 | H | —CH(OH)CH₃ | K | H | 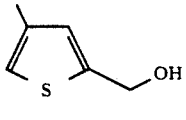 |
| 182 | H | —CH(OH)CH₃ | K | H | 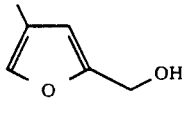 |
| 183 | H | —CH(OH)CH₃ | K | H | 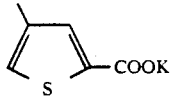 |

TABLE I-continued

| No. | R | R² | M | Rᵃ | HAR-R₂ᵃ |
|---|---|---|---|---|---|
| 184 | H | —CH(OH)CH₃ | K | H | 4-methyl-furan-2-COOK |
| 185 | H | —CH(OH)CH₃ | Na | C(O)NH₂ | 5-methyl-thiophene |
| 186 | H | —CH(OH)CH₃ | Na | C(O)NH₂ | 5-methyl-furan |
| 187 | H | —CH(OH)CH₃ | Na | H | 5-methyl-thiophene-2-C(O)NH₂ |
| 188 | H | —CH(OH)CH₃ | Na | H | 5-methyl-furan-2-C(O)NH₂ |
| 189 | H | —CH(OH)CH₃ | Na | H | thiophene-2-C(O)NH₂ |
| 190 | H | —CH(OH)CH₃ | Na | H | furan-2-C(O)NH₂ |
| 191 | H | —CH(OH)CH₃ | Na | C(O)NH₂ | thiophene |
| 192 | H | —CH(OH)CH₃ | Na | C(O)NH₂ | furan |
| 193 | H | —CH(OH)CH₃ | K | H | thiophene-2-CHO |
| 194 | H | —CH(OH)CH₃ | Na | H | 5-methyl-furan-2-CHO |
| 195 | H | —CH(OH)CH₃ | Na | CH₂OH | 5-methyl-thiophene-2-CH₂OH |

TABLE I-continued

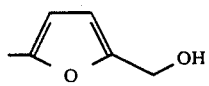

| No. | R | $R^2$ | M | $R^a$ | $HAR-R_2^a$ |
|---|---|---|---|---|---|
| 196 | H | —CH(OH)CH$_3$ | Na | CH$_2$OH | 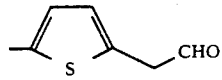 |
| 197 | H | —CH(OH)CH$_3$ | Na | CHO | 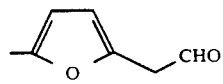 |
| 198 | H | —CH(OH)CH$_3$ | Na | CHO | 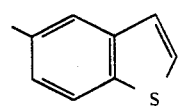 |
| 199 | H | —CH(OH)CH$_3$ | K | H | 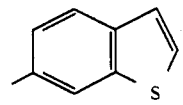 |
| 200 | H | —CH(OH)CH$_3$ | K | H | 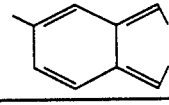 |
| 201 | H | —CH(OH)CH$_3$ | K | H | |

The carbapenem compounds of the present invention are useful per se and in their pharmaceutically acceptable salt and ester forms in the treatment of bacterial infections in animal and human subjects. The term "pharmaceutically acceptable ester or salt" refers to those salt and ester forms of the compounds of the present invention which would be apparent to the pharmaceutical chemist, i.e., those which are non-toxic and which would favorably affect the pharmacokinetic properties of said compounds, their palatability, absorption, distribution, metabolism and excretion. Other factors, more practical in nature, which are also important in the selection, are cost of the raw materials, ease of crystallization, yield, stability, hygroscopicity, and flowability of the resulting bulk drug. Conveniently, pharmaceutical compositions may be prepared from the active ingredients in combination with pharmaceutically acceptable carriers. Thus, the present invention is also concerned with pharmaceutical compositions and methods of treating bacterial infections utilizing as an active ingredient the novel carbapenem compounds of the present invention.

The pharmaceutically acceptable salts referred to above may take the form —COOM. The M may be an alkali metal cation such as sodium or potassium. Other pharmaceutically acceptable cations for M may be calcium, magnesium, zinc, ammonium, or alkylammonium cations such as tetramethylammonium, tetrabutylammonium, choline, triethylhydroammonium, meglumine, triethanolhydroammonium, etc.

The pharmaceutically acceptable salts referred to above may also include non-toxic acid addition salts. Thus, the Formula I compounds can be used in the form of salts derived from inorganic or organic acids. Included among such salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glycoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalene-sulfonate, nicotinate, oxalate, pamoate, pectinate, persulfate, 3-phenylpropionate, picrate, pivalate, propionate, succinate, tartrate, thiocyanate, tosylate, and undecanoate.

The pharmaceutical acceptable esters of the novel carbapenem compounds of the present invention are such as would be readily apparent to a medicinal chemist, and include, for example, those described in detail in U.S. Pat. No. 4,309,438, Column 9, line 61 to Column 12, line 51, which is incorporated herein by reference. Included within such pharmaceutically acceptable esters are those which are hydrolyzed under physiological conditions, such as pivaloyloxymethyl, acetoxymethyl, phthalidyl, indanyl and methoxymethyl, and those described in detail in U.S. Pat. No. 4,479,947, which is incorporated herein by reference.

The novel carbapenem compounds of the present invention may take the form COOM, where M is a readily removable carboxyl protecting group. Such conventional blocking groups consist of known ester groups which are used to protectively block the carboxyl group during the synthesis procedures described above. These conventional blocking groups are readily removable, i.e., they can be removed, if desired, by procedures which will not cause cleavage or other disruption of the remaining portions of the molecule. Such procedures include chemical and enzymatic hydrolysis, treatment with chemical reducing or oxidizing agents under mild conditions, treatment with a transition metal catalyst and a nucleophile, and catalytic hydrogenation. Broadly, such ester protecting groups include alkyl, substituted alkyl, benzyl, substituted benzyl, aryl, substituted aryl, allyl, substituted allyl and triorganosilyl. Examples of specific such ester protecting groups include benzhydryl, p-nitrobenzyl, 2-naphthylmethyl, allyl, 2-chloroallyl, benzyl, t-butyl, 2,2,2-trichloroethyl, t-butyldimethylsilyl, t-butyldiphenylsilyl, trimethylsilyl, 2-(trimethyl)silylethyl, phenacyl, p-methoxybenzyl, acetonyl, o-nitrobenzyl and 4-pyridylmethyl.

The compounds of the present invention are valuable antibacterial agents active against various Gram-positive and to a lesser extent Gram-negative bacteria and accordingly find utility in human and veterinary medicine. The antibacterials of the invention are not limited to utility as medicaments; they may be used in all manner of industry, for example: additives to animal feed, preservation of food, disinfectants, and in other industrial systems where control of bacterial growth is desired. For example, they may be employed in aqueous compositions in concentrations ranging from 0.1 to 100 parts of antibiotic per million parts of solution in order to destroy or inhibit the growth of harmful bacteria on medical and dental equipment and as bactericides in industrial applications, for example in waterbased paints and in the white water of paper mills to inhibit the growth of harmful bacteria.

The compounds of this invention may be used in any of a variety of pharmaceutical preparations. They may be employed in capsule, powder form, in liquid solution, or in suspension. They may be administered by a variety of means; those of principal interest include: topically or parenterally by injection (intravenously or intramuscularly).

Compositions for injection, a preferred route of delivery, may be prepared in unit dosage form in ampules, or in multidose containers. The compositions may take such forms as suspensions, solutions, or emulsions in oily or aqueous vehicles, and may contain formulatory agents. Alternatively, the active ingredient may be in powder form for reconstitution, at the time of delivery, with a suitable vehicle, such as sterile water. Topical applications may be formulated in hydrophobic or hydrophilic bases as ointments, creams, lotions, paints, or powders.

The dosage to be administered depends to a large extent upon the condition and size of the subject being treated as well as the route and frequency of administration, the parenteral route by injection being preferred for generalized infections. Such matters, however, are left to the routine discretion of the therapist according to principles of treatment well known in the antibacterial art. Another factor influencing the precise dosage regimen, apart from the nature of the infection and peculiar identity of the individual being treated, is the molecular weight of the chosen species of this invention.

The compositions for human delivery per unit dosage, whether liquid or solid, may contain from 0.1% to 99% of active material, the preferred range being from about 10-60%. The composition will generally contain from about 15 mg to about 1500 mg of the active ingredient; however, in general, it is preferable to employ a dosage amount in the range of from about 250 mg to 1000 mg. In parenteral administration, the unit dosage is usually the pure compound I in sterile water solution or in the form of a soluble powder intended for solution.

The preferred method of administration of the Formula I antibacterial compounds is parenteral by i.v. infusion, i.v. bolus, or i.m. injection.

For adults, 5-50 mg of Formula I antibacterial compounds per kg of body weight given 2, 3, or 4 times per day is preferred. Preferred dosage is 250 mg to 1000 mg of the Formula I antibacterial given two (b.i.d.) three (t.i.d.) or four (q.i.d.) times per day. More specifically, for mild infections a dose of 250 mg t.i.d. or q.i.d. is recommended. For moderate infections against highly susceptible gram positive organisms a dose of 500 mg t.i.d. or q.i.d. is recommended. For severe, life-threatening infections against organisms at the upper limits of sensitivity to the antibiotic, a dose of 1000 mg t.i.d. or q.i.d. is recommended.

For children, a dose of 5-25 mg/kg of body weight given 2, 3, or 4 times per day is preferred; a dose of 10 mg/kg t.i.d. or q.i.d. is usually recommended.

Antibacterial compounds of Formula I are of the broad class known as carbapenems or 1-carbadethiapenems. Naturally occurring carbapenems are susceptible to attack by a renal enzyme known as dehydropeptidase (DHP). This attack or degradation may reduce the efficacy of the carbapenem antibacterial agent. The compounds of the present invention, on the other hand, are significantly less subject to such attack, and therefore may not require the use of a DHP inhibitor. However, such use is optional and contemplated to be part of the present invention. Inhibitors of DHP and their use with carbapenem antibacterial agents are disclosed in the prior art [see European Patent Applications No. 79102616.4 filed Jul. 24, 1979 (Patent No. 0 007 614); and No. 82107174.3, filed Aug. 9, 1982 (Publication No. 0 072 014)].

The compounds of the present invention may, where DHP inhibition is desired or necessary, be combined or used with the appropriate DHP inhibitor as described in the aforesaid patents and published application. Thus, to the extent that the cited European patent applications 1.) define the procedure for determining DHP susceptibility of the present carbapenems and 2.) disclose suitable inhibitors, combination compositions and methods of treatment, they are incorporated herein by reference. A preferred weight ratio of Formula I compound:DHP inhibitor in the combination compositions is about 1:1. A preferred DHP inhibitor is 7-(L-2-amino-2-carboxyethylthio)-2-(2,2-dimethylcyclopropanecarboxamide)-2-heptenoic acid or a useful salt thereof.

The invention is further defined by reference to the following examples, which are intended to be illustrative and not limiting.

All temperatures are in degrees Celsius.

STARTING MATERIAL SYNTHESES

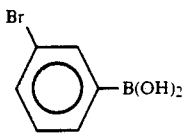

3-BROMOPHENYLBORONIC ACID:

N-Butyllithium (2.5M; 44 mL; 0.11M) was added dropwise over 15 mins. to a vigorously stirred solution of m-dibromobenzene (25 g; 0.106M) in 500 mL of anhydrous ether at −78° under nitrogen. After stirring 10 mins. more, a solution of triisopropylborate (25.3 mL; 0.11M) in anhydrous ether (200 mL) was added over 20 mins. The cooling bath was then removed, and the stirring solution was allowed to warm to R.T. over ~2 hrs. A small amount of solid separated. After stirring 15 mins. more at R.T., 150 mL of ice cold 8% aqueous hydrochloric acid was cautiously added, and the stirring was continued for 15 mins. The organic phase was separated, washed with 2×100 mL of saturated sodium chloride solution, and dried over anhydrous magnesium sulfate. Solvent removal gave ~30 G of crude product as a semi-solid, which was shaken well with 150 mL of hexane. The solid was filtered and washed with 2×25 mL of hexane. The resulting silky solid (mp 178°-9° C. after softening at ~160° C.) (6.5 g) was used as 3-bromophenylboronic acid with a small amount of contamination. The hexane filtrate was concentrated and the residue was stirred well with 150 mL of petroleum ether (30°-60°). The resulting solid was filtered and washed with 2×25 mL of petroleum ether. This resulting solid (4.4 g) melting at 178.3°-179° C. was the desired 3-bromophenylboronic acid.

NMR: 7.38-7.46; 7.70-7.80; 8.1-8.18; 8.31 (aromatic H's)

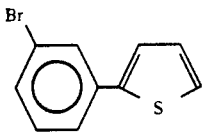

2-(3'-BROMOPHENYL)THIOPHENE:

To a stirred solution of m-bromoaniline (34.4 g; 0.2M) in thiophene (200 mL) was added isoamylnitrite (46.86 g; 0.4M) dropwise over a period of 30 mins. at 0° C. The resulting mixture was cautiously warmed to R.T. and heated to reflux for 16 hours. The reaction mixture was cooled, diluted with 400 mL of ether, washed with 3×100 mL of satd. sodium chloride solution, and dried over anhydrous magnesium sulfate. Solvent and excess thiophene were removed. A solution of the residue in 200 mL of ether was filtered through 50 G silica gel bed. Solvent was removed, and the residue was distilled to give 34% of 2-(3'-bromophenyl)thiophene as a yellow liquid boiling at 130°-2°/~0.2 mm. This liquid solidified on standing in the refrigerator.

NMR: 7.06-7.78

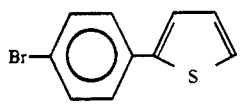

2-(4'-BROMOPHENYL)THIOPHENE:

Similarly, 2-(4'bromophenyl)thiophene was prepared from 4-bromo aniline in 29% yield as a yellow oil boiling at 146°-8°/~0.5 mm.

NMR: ($C_6D_6$): 6.68-6.92 (thiophene H's) 7.03-7.20 (p-phenyl H's).

2-PHENYLTHIOPHENE:

The above method was used to prepare 2-phenylthiophene from aniline in 11% yield as colorless liquid boiling at 110°-113°/~3 mm.

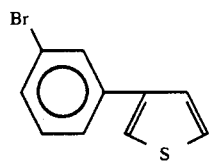

3-(3'-BROMOPHENYL)THIOPHENE:

The thiophene was prepared according to G. Martelli et al., J. Chem. Soc (B)., 901, (1968).

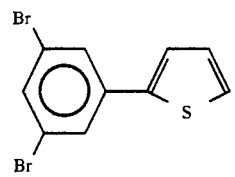

2-(3',5'-DIBROMOPHENYL)THIOPHENE:

3,5-dibromoaniline, upon similar treatment, gave 2-(3',5'-dibromophenyl)thiophene in 55% yield as a yellow oil, which solidified as a glassy solid.

NMR: 7.04-7.68 (aromatic H's)

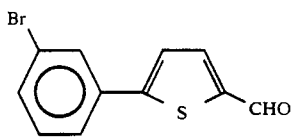

2-FORMYL-5-(3'-BROMOPHENYL)THIOPHENE:

Phosphorus oxychloride (1.15 mL; 15.4 mM) was added slowly to stirring dimethylformamide (0.95 mL; 12.2 mM) at −10° under nitrogen. The resulting mixture was stirred for 15 mins. 2-(3'-bromophenyl)thiophene (2.12 g; 9 mM) was then added. The reaction mixture was then warmed slowly to 110° over a period of 1 hr. cooled and poured into ice, and cautiously neutralized with sodium carbonate. Extraction with ethyl acetate and drying the organic phase with anhydrous magnesium sulfate provided upon concentration 2.16 g of the desired aldehyde as an oily solid.

NMR: 7.26-7.84 (aromatic H's); 9.92(—C(O)H; S)

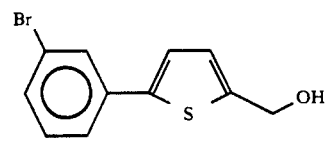

2-(HYDROXYMETHYL)-5-(3'-BROMOPHENYL)THIOPHENE:

Sodium borohydride (400 mg; 10 mM) was added portionwise over 5 min. to a stirred suspension of the above crude aldehyde (2.16 g) in 100 mL of methanol at 0° C. The resulting clear solution was stirred 30 mins. Solvent was then removed in vacuo at R.T. The residue was taken up in 50 mL of ethyl acetate, washed with 3×20 mL of sat'd. sodium chloride solution, and dried over anhyd. magnesium sulfate. Solvent removal followed by silica gel chromatography with methylene chloride gave 1.355 g of desired alcohol as an amorphous solid.

NMR: 1.83 (OH; t; J-6H3); 4.82(CH₂; d; J-6H₃); 6.96-7.75 (aromatic H's)

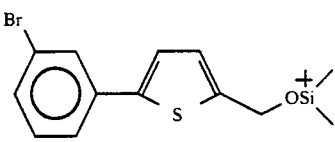

2-(t-BUTYLDIMETHYLSILYLOXYMETHYL)-5-(3'-BROMOPHENYL)-THIOPHENE:

To a stirred solution of 2-(hydroxymethyl)-5-(3'-bromophenyl)thiophene (1.08 G; 4 mM) and triethylamine (1.4 mL; 10 mM) in 20 ml of methylene chloride at R.T. was added t-butyldimethylchlorosilane (1.5 g; 10 mM). This mixture was stirred overnight. diluted with 30 ml of ethyl acetate, washed with 2×15 ml of sat'd. sodium chloride solution, and dried over anhyd. magnesium sulfate. Solvent was removed to give a residue, which was purified on silica gel with ether:petroleum ether (1:20) as solvent mixture. Eluate was distilled to give 0.99 g of 2-(t-butyldimethylsilyloxymethyl)-5-(3'bromophenyl)thiophene as colorless liquid boiling at 167°-170°/~0.2 mm.

NMR: 0.17 & 0.95 (silyl methyls); 4.88 (s, CH₂); 6.88-7.75 (aromatic H's)

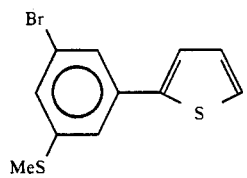

2-[3'-BROMO-5'-METHYLTHIO)PHENYL]THIOPHENE:

2.5M n-butyllithium (1.5 mL; 3.75 mM) was added dropwise to a solution of 2-(3',5'-dibromophenyl)thiophene (1.06 g; 3.33 mM) in anhydrous tetrahydrofuran (7 mL) at −78° under nitrogen. The reaction mixture was then stirred 10 min. and a solution of dimethyldisulfide (0.9 mL; 10 mM) in 3 mL of anhydrous tetrahydrofuran was added. The resulting mixture was stirred overnight at R.T. after which 5 mL of sat'd. ammonium chloride and 20 mL of ethyl acetate were added. The organic phase was separated, washed with 2×10 mL of sat'd. sodium chloride solution, and dried over anhyd. magnesium sulfate. Solvent removal, and purification on silica gel using hexane as solvent gave a liquid, which was distilled to give 52% of 2-[(3'-bromo)-(5'-methylthio)]phenylthiophene as a colorless oil boiling at ~150°-152°/~0.2 mm. (oil bath temp. 180°)

NMR: 1.52(SCH₃; s); 7.00-7.50 (aromatic H's)

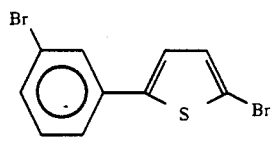

2-BROMO-5-[3'-BROMOPHENYL]THIOPHENE:

A solution of bromine (8 g; 50 mM) in 20 mL of glacial acetic acid was added dropwise to a vigorously stirred solution of 2-(3'-bromophenyl)-thiophene (12 g; 50 mM) in 80 mL of glacial acetic acid. The resulting mixture was heated to reflux 5 hrs, cooled and poured onto ice. A solid separated which was filtered and washed with ice water, and purified on silica gel using hexane as solvent to give 68% of 2-bromo-5-[3'-bromophenyl]thiophene as an amorphous solid.

NMR: 7.00-7.68 (aromatic H's)

3-(3'-BROMOPHENYL)-5-BROMOTHIOPHENE:

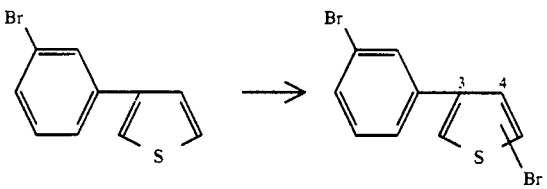

To a solution of 3-(3'-bromophenyl)thiophene, (G. Martelli et al., J. Chem. Soc., (B), 901, 1968) (712 mg, 3 mmol) in acetic acid (6.2 ml) with stirring under N₂, a solution of Br₂ (154 μl, 3 mmol) in acetic acid (4.8 ml) was added dropwise. The resultant orange-red solution was heated for 5 hours at 100° C. After cooling, the reaction mixture was poured into ice water with stirring. A non-filterable milky precipitate was extracted 2X with Et₂O. The combined Et₂O layers were carefully extracted 3X with NaHCO₃ solution and then 2X with brine. After drying (MgSO₄), filtering and concentrating, the residue was chromatographed on a column of Bakers Si Gel (60-200 mesh) packed, applied and eluted with hexane. Those fractions containing the slightly less polar product were combined and concentrated in vacuo (763 mg). Preparative TLC of 663 mg of this material on 7-1000μ Si Gel GF plates (eluting with hexane and extracting with CH₂Cl₂) provided a purer sample of the desired 5-bromo isomer (416 mg) (i.e., less of the undesired 2-bromo isomer was present). Approximately 162 mg of this material was further purified by preparative TLC on 4-1000μ Si Gel GF (eluting and extracting as above) to give 3-(3'-bromophenyl)-5-bromothiophene pure enough for further reaction (196 mg).

MS: m/z 316/318/320 (MI).

¹H NMR (300 MHz, CDCl₃)): δ7.01 (d, J=6 Hz, H₄ of 2-Br compound); 7.23-7.70 (series of m's, phenyl and thiophene protons of the minor 2-Br and the desired 5-Br isomers).

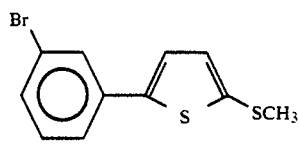

2-METHYLTHIO-5-[3'-BROMOPHENYL]THIOPHENE:

A 2.5M solution of n-butyllithium (2.2 mL; 5.5. mM) was slowly added to a solution of 2-bromo-5-(3'-bromophenyl)thiophene (1.59 g; 5 mM) in 10 mL of tetrahydrofuran at −78° under nitrogen. The mixture was stirred 10 mins. and dimethyldisulfide (1.35 mL; 15 mM) was added slowly. This mixture was stirred overnight at R.T. after which 5 mL of sat'd. ammonium chloride and 15 mL of ethyl acetate were added. The organic phase was separated, washed with 2×5 mL of sat'd. sodium chloride, and dried over anhyd. magnesium sulfate. Solvent removal and purification on silica gel with hexane as solvent gave 2-methylthio-5-(3'-bromophenyl)thiophene as a colorless oil boiling at 142°-5°/0.5 mm.

NMR: 2.54 (SCH$_3$; s); 7.02-7.72 (aromatic H's)

3-(3'-BROMOPHENYL)-5-THIOPHENE CARBOXALDEHYDE:

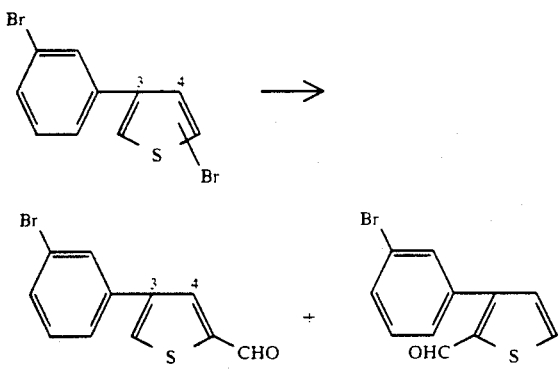

To a solution of the brominated thiophene (mainly the correct 5-bromo isomer; 196 mg, 0.62 mmol) in ether (2.7 ml) at −78° C. under N$_2$, 1.6M BuLi in hexane (388 μl, 0.62 mmol) was added dropwise. After 15 min. at −78°, DMF (63 μl, 0.81 mmol) was added, and the reaction mixture was stirred overnight at ambient temperature. The reaction was partitioned between EA and brine. After phase separation, the organic layer was again extracted with brine, dried, filtered and concentrated to provide crude formylated product (151 mg). Preparative TLC on 3-1000μ Si Gel GF plates (eluting with 20% Et$_2$O/hexane and extracting with CH$_2$Cl$_2$) provided a major band containing a mixture (80 mg) of the desired 5-formyl isomer contaminated with a small amount of the 2-formyl isomer.

MS: m/z 266/268 (MI.)
IR(CH$_2$Cl$_2$): 1670 (formyl) cm$^{-1}$
$^1$H NMR (300 MHz, CDCl$_3$): δ7.22 (low amplitude d, J=5 Hz, H$_4$ of minor amount of 2-formyl); 7.29-8.00 (series of m's phenyl & thiophene protons); 9.88 (d, J=1 Hz, long range splitting minor amount of 2-formyl); 9.98 (d, J=1 Hz, CHO of 5-formyl, allylic splitting).

3-[(3'-BROMOPHENYL)-(5-HYDROXYMETHYL)]THIOPHENE

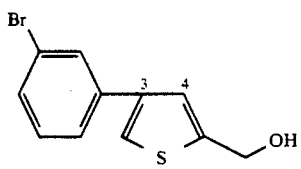

To a solution of the formylated thiophene (79 mg, 0.3 mmol) stirred in MeOH (3 ml) at 0°, NaBH$_4$ (13.6 mg, 0.34 mmol) was added, and stirring was continued for 40 min. Upon concentration to an oil under a N$_2$ stream, the residue was partitioned between EA and brine, the organic layer was again washed with brine, dried, filtered and concentrated in vacuo to give the crude product (77 mg). Preparative TLC on 2-1000μ Si Gel GF plates (eluting with CH$_2$Cl$_2$ and extracting the major UV band with 10% MeOH/CH$_2$Cl$_2$) provided the purified 5-hydroxymethyl compound (70 mg, 88% yield). A small amount of faster running material (5 mg, 6% yield) proved to be the undesired 2-hydroxymethylthiophene compound having the widely split H4-doublet (J=4.5 Hz). The desired product contained none of this impurity.

MS: m/z 268/250(MI)
IR(CHCl$_2$): 3600(OH) cm$^{-1}$
$^1$H NMR (300 MHz, CDCl3): δ1.84 (t, J=6 Hz, OH); 4.85(dd, J=0.5 (allylic coupling to H$_4$) and 6 Hz; CH$_2$OH); 7.24, 7.42, 750 and 7.70 (4 sets of m's; phenyl and thiophene H's).

NMR data for the less polar 2-hydroxymethylthiophene (5 mg above):
$^1$H NMR (300 mHz, CDCl$_3$): δ1.81 (t, J=6 Hz, OH); 4.82 (d, J=6 Hz, CH$_2$OH); 4.86 (br d, J=6 Hz, CH$_2$OH of small amount of 5-isomer); 7.08 (d, J=5 Hz, H$_4$); 7.25-7.71 (series of multiplets, phenyl and thiophene protons).

3-(3'-BROMOPHENYL)-5-(t-BUTYLDIMETHYLSILYLOXYMETHYL)THIOPHENE:

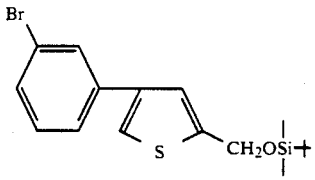

To a solution of the 5-hydroxymethyl thiophene (62 mg, 0.23 mmol) in CH$_2$Cl$_2$ (1.1 ml) at 0° C. with stirring under N$_2$, TBDMSiCl (183 mg, 0.55 mmol) and Et$_3$N (80 μl, 0.59 mmol) were added. The cooling bath was removed, and the reaction mixture was stirred overnight at ambient temperature. Work-up of an aliquot showed incomplete conversion. Therefore, DMF (20 μl) in CH$_2$Cl$_2$ (1 ml) was added, and stirring was resumed for a few hours*. Brine containing 1M K$_2$HPO$_4$ (1 ml) and additional CH$_2$Cl$_2$ were added to the reaction mixture with stirring. After phase separation, the aqueous layer was again extracted with CH$_2$Cl$_2$, and the combined organic layers were washed with brine, dried, filtered and concentrated in vacuo to give the crude product (97 mg). Preparative TLC on 2-1000μ Si Gel GF plates (eluting with 20% Et$_2$O/hexane and extracting with CH$_2$Cl$_2$) provided the purified 5-silyloxymethyl thiophene (79 mg, 90% yield).

*In later runs, the DMF was introduced initially [i.e., starting material (820 mg); CH$_2$Cl$_2$ (10.5 ml); TBDMSiCl (820 mg); Et$_3$N (788 μl); DMF (830 μl)]and overnight reaction provided complete silylation.

MS: m/z 325/327 (MI-t-butyl); 251/253 (MI-OTBDMSi).

$^1$H NMR (300 MHz, CDCl$_3$): δ0.13 (s, Si(CH$_3$)$_2$); 0.94 (s, t-butyl-Si); 4.89 (s, CH$_2$OTBDMSi); 7.16-7.70 (series of m's, phenyl and thienyl H's).

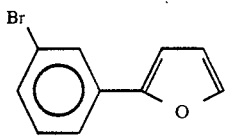

2-(3'-BROMOPHENYL)FURAN:
BP: 98°-105°/0.1 mm
Reference: E. L. Plummer, J. Agric. Food Chem., 31, 718-721 (1983).

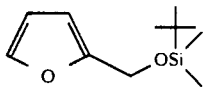

2-(t-BUTYLDIMETHYLSILYLOXYMETHYL)-FURAN:

To a stirring mixture of 2-furan methanol (33 g, ~0.335M) and triethylamine (47 mL, ~0.335M) in anhydrous methylene chloride (200 mL) under nitrogen was added t-butyldimethylchlorosilane portionwise at room temperature. 20 mL of N,N-dimethylformamide was added. The resulting mixture was stirred 3 hrs. After dilution with 400 mL of ether, the reaction mixture was washed with 3×100 mL of ice-water, 100 mL of saturated sodium chloride solution, and dried over anhydrous magnesium sulfate. Solvent removal gave a crude product, which was distilled to afford 39.8 g of the desired silyl ether as a colorless liquid boiling at 76°-7°/~0.5 mm.

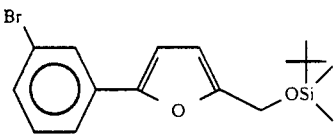

2-(3'-BROMOPHENYL)-5-(t-BUTYLDIMETHYLSILYLOXYMETHYL)-FURAN:

To a stirred solution of m-bromoaniline (6.88 g; 0.04M) in 42.2 g (0.2M) of 2-(t-butyldimethylsilyloxymethyl)furan at 0° was added isoamylnitrite (10.75 mL; 0.08M) dropwise over a period of 0.5 hr. The resulting mixture was then heated 16 hours at 50° C. The reaction mixture was cooled and diluted with 150 mL of ether and washed with 2×100 mL of ice cold water. The organic phase was dried over anhydrous magnesium sulfate, and the residue was distilled after filtering through 50 G of silica gel bed, to give 26% of the desired 2-(3'-bromophenyl)-5-(t-butyldimethylsilyloxymethyl)-furan as a colorless liquid boiling at 163°-7°/~0.5 mm.

STEP A: GENERAL SYNTHESIS OF ARYLKETONES:

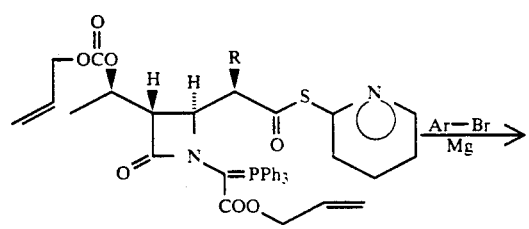

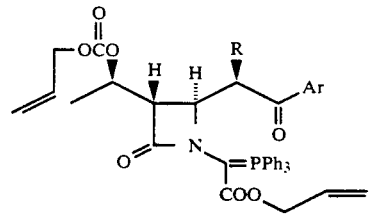

METHOD 1:

Aryl bromide (1 mM) was added to a stirred suspension of magnesium chips (1.25 mM) in 2 mL of anhydrous tetrahydrofuran under nitrogen at R.T. 8 μL of 1,2-dibromoethane was then added. The resulting mixture was stirred 3 hours, when most of the metal was digested. The resulting dark yellow solution was used as 0.5M solution of the aryl Grignard reagent.

This Grignard reagent solution was added dropwise to a stirred solution of (3S,4R)-1-[[(allyloxy)carbonyl](-triphenylphosphoranylidene)-methyl]-3-[(1R)-1-[(allyloxy)carbonyloxy]ethyl]-4-[[2'-pyridylthio)carbonyl]-methyl]azetidin-2-one, (~0.5 mM) in 2 mL of anhydrous tetrahydrofuran at 0° under nitrogen. The reaction mixture was stirred 15 mins at 0°. Satd ammonium chloride solution (5 mL) and 10 mL of ethyl acetate were added. The organic layer was separated, and washed with 2×5 mL of satd sodium chloride solution and dried over anhyd. magnesium sulfate. Solvent removal followed by silica gel chromatography using mixtures (1:1 to 2:1) of ethyl acetate:hexane as eluant gave the desired ylid arylketone as a pale yellow foam.

METHOD 2:

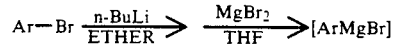

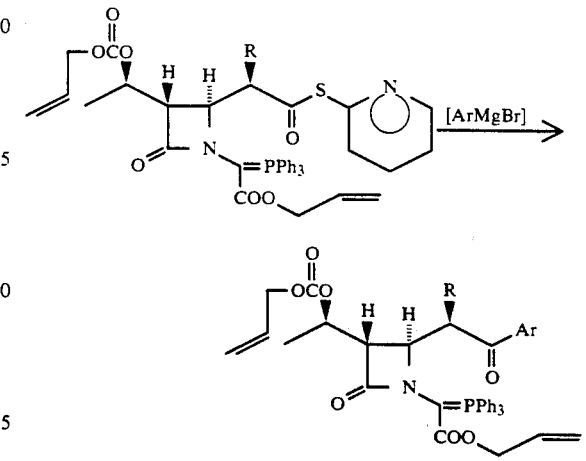

To a stirred solution of 3 mM aryl bromide in anhydrous ether (12 mL) at −78° under nitrogen was added n-butyllithium (2.5 molar solution; 1.32 mL; 3.3 mM) dropwise. The resulting mixture was stirred 0.5 hr. A solution of magnesium bromide, freshly prepared by stirring 6.6 mM of magnesium turnings in 24 mL of anhydrous tetrahydrofuran with 6 mM of 1,2-dibromoethane for about 1 hr under nitrogen at ambient temperature, was then added dropwise to the above stirring lithium salt at −78°. The resulting mixture was stirred 15 mins at −78°, and 30 mins at 0°. The thus obtained turbid solution was used as a 0.0833 molar solution of the required aryl magnesium bromide.

This solution of the Grignard reagent was added slowly to a stirred solution of 1.4 mM of (3S,4R)-1-[[allyloxy)carbonyl](triphenylphosphoranylidene)methyl]-3-[(1R)-1-[(allyloxy)carbonyloxy]ethyl]-2-[[(2'-pyridylthio)carbonyl]methyl]azetidin-2-one, in 5 mL of anhydrous tetrahydrofuran at 0° under nitrogen. The reaction mixture was stirred 15 mins. at 0°, and satd. ammonium chloride (15 mL) and 30 mL of ethyl acetate were added. The organic layer was separated, washed with 2×15 mL of sat'd. sodium chloride solution, and dried over anhydrous magnesium sulfate. Solvent removal and purification on silica gel using a (1:1 to 2:1) mixture of ethyl acetate:hexane gave the desired aryl ketone, as a light yellow foam.

STEP B: GENERAL PROCEDURE FOR CYCLIZATION:

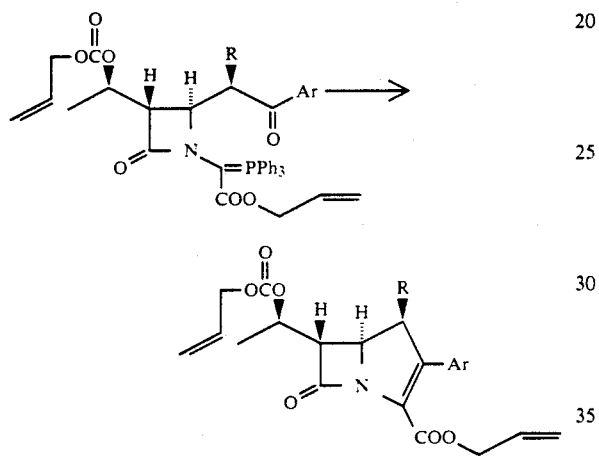

A solution of the ylid ketone (0.25 mM) in 2 mL of p-xylene containing a tiny crystal of hydroquinone was heated 45 mins. to 3 hours (depending on the nature of R) at 130° C. under nitrogen. The solution was cooled, applied in a suitable solvent to a silica gel column packed with hexane and then eluted first with hexane and then with 4:1 to 2:3 mixtures of hexane:ethyl acetate to give the desired carbapenem analogs.

STEP C: GENERAL PROCEDURE FOR DEALLYLATION:

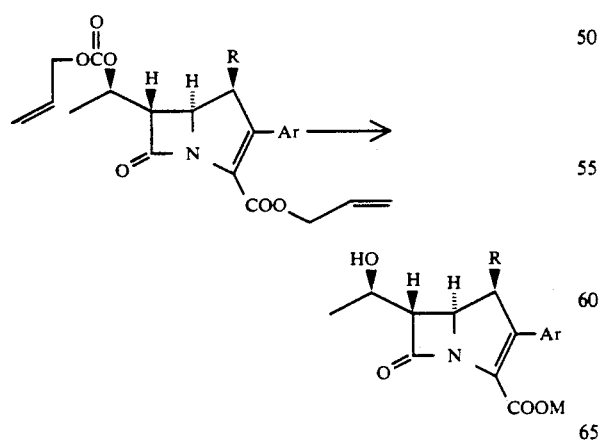

To a stirred solution of the carbapenem (0.2 mM) in 3 mL of a 1:1 mixture of methylene chloride:ether in a centrifuge tube at 0° under nitrogen were added 2-ethylhexanoic acid (0.2 mM), triphenylphosphine (0.05 mM), tetrakis-(triphenylphosphine)-palladium (0.04 mM), and 0.2 mM of sodium or potassium 2-ethylhexanoate. This mixture was stirred 2 hrs when a solid precipitated out. After diluting with 10 mL of ether, the mixture was centrifuged and the supernatant liquid was decanted. The remaining solid was stirred with 2 mL of ethyl acetate and centrifuged. The resulting solid was dissolved in 1 mL of water and applied to a 1000μ reverse phase silica gel plate. Elution with mixtures of acetonitrile:water or EtOH:water gave an ultraviolet active area, which was scraped and stirred with 5 mL of 4:1 acetonitrile:water mixture. The solid was filtered and washed with 3×2 mL of a 4:1 acetonitrile:water mixture. The filtrate was washed with 4×10 mL of hexane, concentrated to 1 mL in vacuo at R.T. and lyophilized to give the sodium or potassium salt of the carbapenem as a white to creamy, fluffy mass.

In the following examples:
the IR data are in cm$^{-1}$;
the UV data are in nanometers for $\lambda_{max}$ water; and
the NMR spectra are measured in CDCl$_3$ solvent unless otherwise specified.

EXAMPLE 1

| STEP A | |
|---|---|
| | Ar—Br = 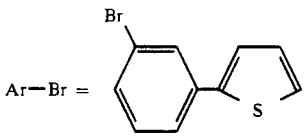 |
| Conditions A: | 1) ~1 hr.; R.T.; Mg/THF |
| | 2) 0°; 15 min; THF; pyridylthioester |
| Yield: | 54% |
| STEP B | |
| Conditions: | Xylene; 135°; 1.5 hrs. |
| Yield: | 79% |
| Spectra: | |
| IR: | 1780; 1740; 1720 |
| NMR: | H6: 3.41–3.47; dd; J=3 & 8.5 Hz |
| | H5: 4.24–4.35; ddd; J=3, 8.5 & 10 Hz |
| STEP C | |
| M− = K− | |
| Conditions: | PPh$_3$; Pd(PPh$_3$)$_4$; |
| | 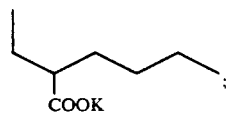 |
| | 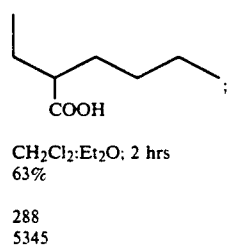 |
| | CH$_2$Cl$_2$:Et$_2$O; 2 hrs |
| Yield: | 63% |
| Spectra: | |
| UV: | 288 |
| ε ext: | 5345 |

EXAMPLE 2

STEP A

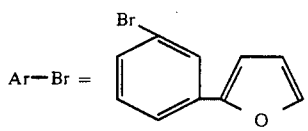

| Conditions: | 1) 1 hr.; R.T.; Mg/THF |
| --- | --- |
| | 2) 0°; 15 min; THF; pyridylthioester |
| Yield: | 76% |
| Spectra | |
| IR: | 1745; 1680; 1615 |

STEP B

| Conditions: | Xylene. 136-8°; 1.5 hrs. |
| --- | --- |
| Yield: | 50% |
| Spectra | |
| IR: | 1780; 1740; 1718 |
| NMR: | H6: 3.42-3.48; dd; J = 3 & 8 Hz |
| | H5: 4.25-4.36; ddd; J = 3, 10 & 9 Hz |

STEP C

M⁻ = K⁺

Conditions: Pd(PPh₃)₄; Ph₃

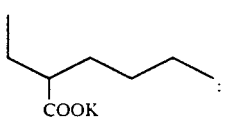

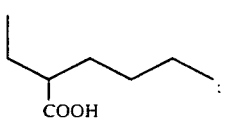

| | CH₂Cl₂:Et₂O; 2 hrs. |
| --- | --- |
| Yield | 42% |
| Spectra: | |
| UV: | 281 |

EXAMPLE 5

STEP A

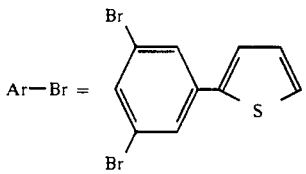

| Conditions | |
| --- | --- |
| | 1) BuLi/THF: −78° |
| | 2) MgBr₂; THF |
| | 3) 0°; 30 min; pyridylthioester |
| Yield: | 57% |
| Spectra: | |
| IR: | 1745; 1685; 1650; 1620 |

STEP B

| Conditions: | Xylene; 130°; 2.5 hrs. |
| --- | --- |
| Yield: | 60% |
| Spectra: | |
| IR: | 1785; 1740; 1720 |
| NMR: | H6: 3.4-3.5; dd; J = 3 & 8 Hz |
| | H5: 4.24-4.38; ddd; J = 3, 9 & 10 Hz |

STEP C

Conditions: Pd(PPh₃)₄; PPh₃

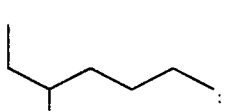

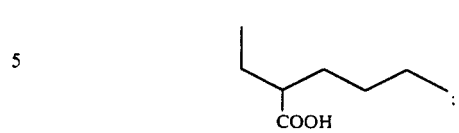

| Spectra: | |
| --- | --- |
| UV: | 292 |

EXAMPLES 9, 11, 13

STEP A

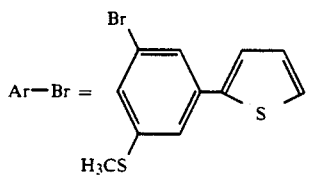

| Conditions: | 1) BuLi/THF; −78° |
| --- | --- |
| | 2) MgBr₂; THF |
| | 3) 0°; 30 min; pyridylthioester |
| Yield: | 29% |
| Spectra: | |
| IR: | 1745; 1685; 1650; 1625 |

STEP B

| STEP B1: | CYCLIZATION OF YLIDE KETONE TO CARBAPENEM |
| --- | --- |
| STEP B2: | OXIDATION OF SULFIDE TO SULFOXIDE |
| STEP B3: | OXIDATION OF SULFIDE TO SULFONE |
| Conditions B1: | Xylene; 130°; 2 hrs. |
| Yield: | 75% |
| Spectra: | |
| IR: | 1780; 1745; 1720 |
| NMR: | H6: 3.4-3.46; dd; J = 3 & 8 Hz |
| | H5: 4.24-4.36; ddd; J = 3, 9 & 10 Hz |
| Conditions B2: | mCPBA; 1.5 eq.; NaHCO₃; 0°; 1 hr. CH₂Cl₂; workup with Na₂S₂O₃; purification on silica gel |
| Yield: | 53% (sulfoxide) |
| Spectra: | |
| IR: | H6: 3.43-3.80; dd; J = 3 & 8 Hz |
| | H5: 4.27-4.38; ddd; J = 3, 9 & 10 Hz |
| Conditions B3: | mCPBA; 2.5 eq.; NaHCO₃; 0°; 1 hr; CH₂Cl₂ |
| Yield: | 74% (sulfone) |
| Spectra: | |
| IR: | 1780; 1740; 1720 |
| NMR: | H6: 3.46-3.52; dd; J = 3 & 8 Hz |
| | H5: 4.3-4.41; ddd; J = 3, 9 & 10 Hz |
| | SCH₃: 3.12(s) |

STEP C

M⁺ = Na⁺

Conditions: PPh₃; Pd(PPh₃)₄;

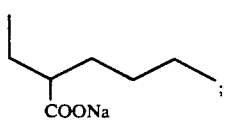

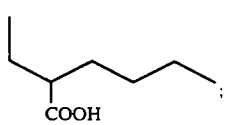

| | CH₂Cl₂:Et₂O; 0°; 2.5 hrs. |
| --- | --- |
| Yield: | 17% of sulfide 9 from Step B1 |

Spectra:
UV: 295
ε ext: 2820
Yield: 62% of sulfoxide 11 from Step B2
Spectra:
UV: 295
ε ext: 7343
Yield: 73% of sulfone 13 from Step B3
Spectra:
UV: 296
ε ext: 7280

EXAMPLE 17

STEP A

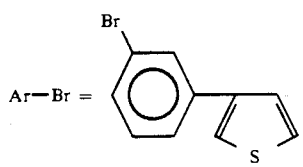

Conditions: 1) Mg/THF; 1 hr.; R.T.
 2) 0°; 15 min; THF; pyridylthioester
Yield 57%
STEP B
Conditions: Xylene; 130°; 2 hrs.
Yield % 49%
Spectra
IR: 1780; 1740; 1720
NMR: H6: 3.42–3.47; dd; 3 & 8.5Hz
 H5: 4.23–4.36; ddd; 3, 8.5 & 9.5Hz

STEP C
M⁻ = K⁻
Conditions: PPh₃; Pd(PPh₃)₄;

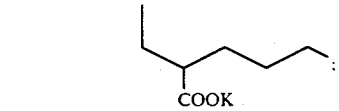

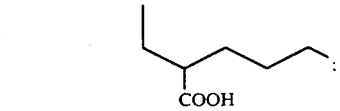

Yield: 36%
UV: 300
ε ext 5365

EXAMPLES 35 & 37

STEP A
STEP A1: PREPARATION OF YLTIDE KETONE
STEP A2: DESILYLATION OF SILYL ETHER
STEP A1:

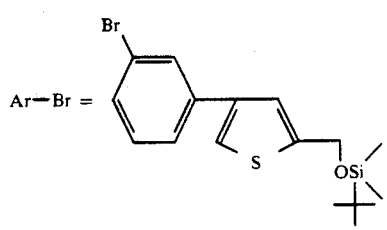

Conditions: 1) Mg/THF; 3 hr./R.T.
 2) 0°; 15 min; THF; pyridylthioester
Yield: 67%
STEP A2:
Conditions: CH₃OH/H₂SO₄;
 0°; 1.25 hrs
Yield: 81%
STEP B
STEP B1: CYCLIZATION OF YLIDE KETONE TO CARBAPENEM
STEP B2: OXIDATION OF CARBINOL TO ALDEHYDE
Conditions
B1: Xylene; 130°; 1.5 hrs.
Yield: 83%
Conditions:
B2: Powdered 3Å mol. sieves; N-methyl morpholine N-oxide; Tetra(n-propyl)ammonium perruthenate; methylene chloride; 15 mins; R.T.; filter through silica gel and evaporate solvent.
Yield: 15%
Spectra:
IR: 1780; 1745; 1720
STEP C
STEP C1: DEALLYLATION OF CARBINOL TO EXAMPLE 35
STEP C2: DEALLYLATION OF ALDEHYDE TO EXAMPLE 37
M⁻ = K⁻
Conditions: PPh₃; Pd(PPh₃)₄;
C1:

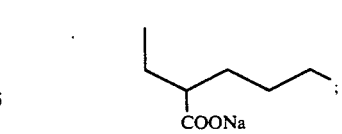

CH₂Cl₂:Et₂O; 2 hours
Yield: 36% of 35
Spectra:
UV: 302
ε ext 4030
Conditions: M⁻ = Na⁻
C2:
PPh₃; Pd(PPh₃)₄

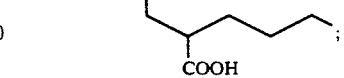

CH₂Cl₂; ether; 2 hrs
Yield: 28% of 37
Spectra:
UV: 333
ε ext 2025

EXAMPLE 36

STEP A

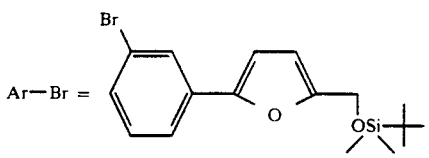

| Conditions: | 1) ~1 hr; R.T.; Mg/THF |
| --- | --- |
| | 2) 0°; 15 min.; THF; pyridylthioester |
| Yield: | 45% |

STEP B

| STEP B1: | FORMATION OF CARBAPENEM FROM YLIDE KETONE |
| --- | --- |
| STEP B2: | DESYLILATION OF SILYLETHER TO THE CARBINOL |

Conditions:
| B1 | Xylene; 136-8°; ~1.5 hrs. |
| --- | --- |
| Yield: | 56% |

Spectra:
| IR: | 1780; 1740; 1720 |
| --- | --- |
| NMR: | H6: 3.38-3.44; dd; J=3 & 8Hz |
| | H5: 4.22-4.34; ddd; J=3, 9 & 10Hz |

Conditions:
| B2: | n-Bu4NF; AcOH; THF; 3 hrs; 0° |
| --- | --- |
| Yield: | 32% |

Spectra
| NMR: | H6: 3.41-3.47; dd; J=3 & 8Hz |
| --- | --- |
| | H5: 4.23-4.35; ddd; J=3, 9 & 10Hz |

STEP C

M— = K—

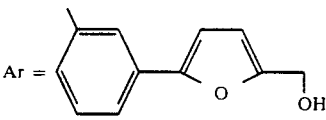

Conditions PPh3; Pd(PPh3)4;

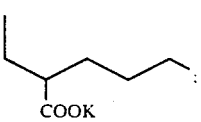

| | CH2Cl2:Et2O; 2 hrs. |
| --- | --- |
| Yield: | 27% |

Spectra
| UV: | 300 |
| --- | --- |

EXAMPLE 60

STEP A

| STEP A1: | PREPARATION OF YLIDE KETONE |
| --- | --- |
| STEP A2: | DESILYATION OF SILYL ETHER TO CARBINOL |

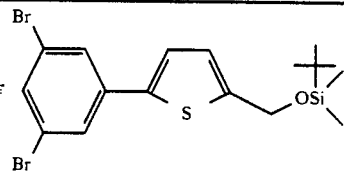

Conditions:
| A1: | 1) Mg/THF; 3 hrs.; R.T. |
| --- | --- |
| | 2) 0°; 15 min; pyridylthioester |
| Yield: | 23% of ylide ketone |

Spectra:
| IR: | 1740; 1690; 1645; 1620 |
| --- | --- |
| A2: | CH3OH; H2SO4 |
| Yield: | 72% of carbinol |

Spectra:
| IR: | 3100(OH); 1740; 1685; 1620 |
| --- | --- |

STEP B

Conditions: Xylene; 130°; 3 hrs.
| Yield | 81% |
| --- | --- |

Spectra:
| IR: | 3500(OH); 1740; 1720 |
| --- | --- |
| NMR: | OH: 1.96-2.06; t; J=6 Hz |
| | CH2O: 4.80-4.86; d; J=6 Hz |
| | H6: 3.40-3.49; dd; J=3 & 8 Hz |
| | H5: 4.24-4.38; ddd; J=3, 8.5 & 9.5 Hz |

STEP B

Conditions: PPh3; Pd(PPh3)4;

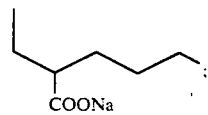

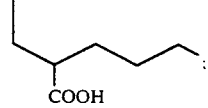

| | CH2Cl2:Et2O; 0°; 2 hrs. |
| --- | --- |
| Yield: | 63% |

Spectra:
| UV: | 296 |
| --- | --- |
| ε ext: | 5638 |

EXAMPLES 120, 122 & 124

STEP A

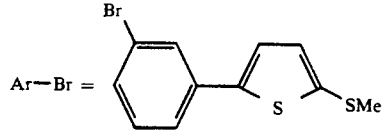

Conditions:
| | 1) BuLi/THF; −78° |
| --- | --- |
| | 2) MgBr2; THF |
| | 3) 0°; 30 min; pyridylthioester |
| Yield: | 69% |

STEP B

| STEP B1: | CYCLIZATION OF YLIDE KETONE TO CARBAPENEM |
| --- | --- |
| STEP B2: | OXIDATION OF SULFIDE TO SULFOXIDE AND SULFONE |

Conditions:
| B1: | Xylene; 130°; 2.5 hrs. |
| --- | --- |
| Yield: | 94% |

Spectra:
| NMR: | H6: 3.4-3.48; dd; J=3 & 8.5 Hz |
| --- | --- |
| | H5: 4.24-4.37; ddd; J=3, 9 & 10 Hz |
| | SCH3: 2.53(s) |

-continued

| | |
|---|---|
| Conditions: | |
| B2: | mCPBA; NaHCO$_3$; CH$_2$Cl$_2$ 0°; 1 hr; workup with Na$_2$S$_2$O$_3$; purification on silica gel |
| Yield: | 49% (sulfoxide) |
| Spectra: | |
| NMR: | H6: 3.40–3.49; dd; J=3 & 8.5 Hz<br>H5: 4.25–4.39 ddd; J=3, 9.5 & 10 Hz<br>SCH$_3$: 2.96(s) |
| Yield: | 28% (sulfone) |
| Spectra: | |
| IR: | 1780; 1745; 1725 |
| NMR: | H6: 3.43–3.51; dd; J=3 & 8.5 Hz<br>H5: 4.26–4.40; ddd; J=3, 9 & 10 Hz<br>SCH$_3$: 3.22(s) |
| STEP C | |
| M$^-$ = Na$^+$ | |
| Conditions: | PPh$_3$; Pd(PPh$_3$)$_4$; |

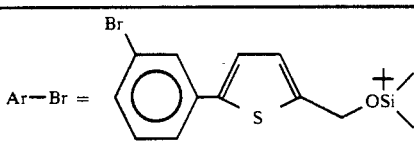

| | |
|---|---|
| | CH$_2$Cl$_2$:Et$_2$O; 0°; 2 hrs. |
| Yield: | 8% of sulfide (120) from Step B1 |
| UV: | 308 |
| ε ext: | 5584 |
| Spectra: | |
| Yield: | 54% of sulfoxide (122) from Step B2 |
| UV: | 301 |
| ε ext: | 8301 |
| Yield: | 45% of sulfone (124) from Step B2 |
| Spectra: | |
| UV: | 298 |
| ε ext: | 6006 |

EXAMPLES 181, 183 & 193

Ar—Br = (structure: bromophenyl-thienyl-CH=CH-CH$_2$-OSi)

| | |
|---|---|
| STEP A | |
| STEP A1: | PREPARATION OF THE YLIDE SILYLETHER KETONE |
| Conditions: | 1) Method A: Mg (2.2 eq); Br-CH$_2$-CH$_2$-Br (1.2 eq); THF; reflux; 3 hrs<br>2) Pyridylthioester; THF; 0°; 1.5 hrs |
| Yield: | 53% |
| Spectra: | |
| MS: | m/z 901(MI); 262 (Ph$_3$P) |
| IR(CH$_2$Cl$_2$): | 1740 (carbonyl); 1620 (ylid) cm$^{-1}$ |
| $^1$H NMR | (300MHz, CDCl$_3$): selected absorbances δ 0.14 (s, Si(CH$_3$)$_2$); 0.94 (s, t-butyl Si); 1.16 (d, J=6 Hz, CH$_3$CHO—); 2.79 (dd, H$_6$); 4.90 (s, CH$_2$OSi—); 5.75–6.00 (m, two CH$_2$CH=CH$_2$); 7.11–8.21 (all aromatic protons) |

STEP A2: DESILYLATION OF THE YLIDE SILYLETHER KETONE TO YLIDE ALCOHOL KETONE

A solution of the arylketone (from Step A1) (116 mg, mmol) was dissolved in 0.2N HCl in 9:1 MeOH:H$_2$O (5.4 ml) at 0° with stirring under N$_2$. After 1 h at 0°, the reaction mixture was added to 2.7 ml 1M K$_2$HPO$_4$; 1.6 ml 1M KH$_2$PO$_4$, H$_2$O and EA and shaken well. Upon phase separation, the aqueous phase was again extracted with EA, and the combined organic layers were washed with brine, dried, filtered (MgSO$_4$) and concentrated in vacuo. Preparative TLC on 2-1000μ Si Gel GF plates (eluting with 50% EA/CH$_2$Cl$_2$ and extracting with 10% MeOH/CH$_2$Cl$_2$) provided the purified hydroxymethyl arylketone (82 mg, 80%).

MS m/z 787 (MI); 509 (MI—Ph$_3$P=O); 262 (Ph$_3$P)
IR 2965 (CH$_2$Cl$_2$): 3600 (OH); 1740 (carbonyls); 1620 (ylid) cm$^{-1}$.

$^1$H NMR (300 MHz, CDCl$_3$): δ selected absorbances 1.15 (d, J=6 Hz, CH$_3$CHO—); 2.78 (dd, J=2 & 10 Hz, H$_6$); 4.87 (s, CH$_2$OH); 5.74–6.00 (m, two CH$_2$—CH=CH$_2$).

STEP A3: OXIDATION OF ALCOHOL TO ACID AND PROTECTION AS ALLYLESTER

A solution of the hydroxymethyl arylketone from Step A2 (54 mg, 0.07 ml) in acetone (0.7 ml) with stirring at 0° was treated with Jones reagent, 2.6M in CrO$_3$ (35 μl, 0.09 mmol). After 20 min., a second equivalent amount of Jones reagent was added, and stirring was continued for 15 min. Upon removal of the cooling bath, stirring was continued for 30 min., and then isopropanol (30 μl) was added. After 5 mins., Na$_2$SO$_4$ was added, and the reaction mixture was stirred, then filtered, and the insoluble residue washed well with CH$_2$Cl$_2$. The filtrate was concentrated in vacuo and chased a few times with toluene to provide a yellow foam. The foam was chromatographed on a small column of Si Gel packed and applied in CH$_2$Cl$_2$ and then eluted with 0.5% HAc/CH$_2$Cl$_2$. The desired fractions were concentrated in vacuo and chased repeatedly with toluene to give the purified carboxylic acid (54 mg, 98% yield). The acid was immediately dissolved in DMF (0.8 ml) and stirred with DIEA (17.3 μl, 0.1 mmol) and allyl bromide (8.6 μl, 0.1 mmol) under N$_2$. After 1 h, an additional amount of DIEA (35 μl, 0.2 mmol) and allyl bromide (17 μl, 0.2 mml) was added, and the reaction mixture was stirred for an additional few hours. The reaction mixture was concentrated in vacuo, and the residue was partitioned between ethyl acetate (EA), 1M K$_2$HPO$_4$ (1 ml) and 1M KH$_2$PO$_4$ (1 ml) and then washed with brine, dried (MgSO$_4$), filtered and concentrated in vacuo to provide crude product (46 mg). Preparative TLC on 2-1000μ Si Gel GF plates (eluting with 20% EA/CH$_2$Cl$_2$ and extracting with 10% MeOH/CH$_2$Cl$_2$) provided the purified allylated arylketone (35 mg, 63% yield).

R$_f$ on Si gel analytical plates (eluant=0.5% HAc/CH$_2$Cl$_2$); R$_f$ (acid)=0.3, (eluant=20% EA/CH$_2$Cl$_2$); R$_f$(allylester)=0.8.

STEP B
STEP B1: CYCLIZATION OF YLIDE SILYLETHER KETONE FROM STEP A1 TO THE CARBAPENEM
STEP B2: DESILYLATION OF CARBAPENEM SILYLETHER
STEP B3: OXIDATION OF CARBINOL TO ALDEHYDE
STEP B4: CYCLIZATION OF DIESTER FROM STEP A3 TO CARBAPENEM
B1:
Conditions: Xylene; reflux; 1 hr
Yield: 80%

Spectra:

$^1$H NMR (300 MHz, CDCl$_3$): δ0.14 (s, Si(CH$_3$)$_2$); 0.95 (s, t-butyl-Si); 1.49 (d, J=6 Hz, C$\underline{H}_3$CHO—); 3.22 (dd, J=10 & 18 Hz, H$_{1a}$); 3.32 (dd, J=8 & 18 Hz, H$_{1b}$); 3.42 (dd, J=3 & 8 Hz, H$_6$); 4.30 (m, H$_5$); 4.50-4.74 (m, two C$\underline{H}_2$CH=CH$_2$); 4.88 (s, C$\underline{H}_2$OTBDMSi); 5.11-5.40 (m, two CH$_2$CH=C$\underline{H}_2$); 5.76-601 (m, two CH$_2$—C$\underline{H}$=CH$_2$); 7.16-7.53 (m's, phenyl and thienyl protons).

B2:

To a solution of the cyclized material (12 mg, 0.02 mmol) in THF (0.6 ml) with stirring at 0° under N$_2$, 1M Bu$_4$NF in THF (80 μl, 0.08 mmol) and acetic acid (14 μl, 0.24 mmol) were added. The reaction mixture was stirred for 1 hr at ambient temperature. Both EA and H$_2$O were added to the reaction mixture. After phase separation, the aqueous layer was extracted again with EA. The combined organic layer was washed with brine, dried (MgSO$_4$), filtered and concentrated in vacuo to provide the crude product (11 mg). Preparative TLC on 1-1000μ Si Gel GF plate (eluting with 50% EA/hexane and extracting with 10% MeOH/CH$_2$Cl$_2$) provided the purified hydroxymethyl carbapenem (3.5 mg, 35% yield).

IR(CH$_2$Cl$_2$): 1780 (β-lactam); 1740 & 1715 (carbonate and ester) cm$^{-1}$.

$^1$H NMR (300 MHz, CDCl$_3$): δ1.49 (d, J=6 Hz, C$\underline{H}_3$CHO—); 1.85 (t, J=6 Hz, OH); 3.13 (dd, J=10 and 18 Hz, H$_{1a}$); 3.32 (dd, J=9 & 18 Hz, H$_{1b}$); 3.43 (dd, J=3 & 8 Hz, H$_6$); 4.59-4.74 (m's, two C$\underline{H}_2$CH=CH$_2$); 4.88 (d, J=6 Hz, C$\underline{H}_2$OH); 5.13-5.40 (m, two CH$_2$CH=C$\underline{H}_2$); 5.76-6.01 (m, two CH$_2$C$\underline{H}$=CH$_2$); 7.24-7.55 (m's, phenyl and thienyl protons)

B3:

To a solution of the hydroxymethyl carbapenem from Step B2 (70 mg, 0.14 mmol) in sieved CH$_2$Cl$_2$ (1.8 ml) with stirring (drying tube), 4-methylmorpholine-N-oxide (24 mg, 0.2 mmole) and 20 mg powdered 3 Å molecular sieves (previously activated at 110°) were added. Stirring was continued for 10 min., after which tetrapropyl ammonium perruthenate (5.7 mg, 0.02 mmol) was added, and the reaction mixture was stirred for 20 min at ambient temperature. The entire reaction mixture was then filtered through a column of 8 g Bakers Si Gel (60-200 mesh) packed in CH$_2$Cl$_2$ and eluted with 10% EA/CH$_2$Cl$_2$ to provide the purified formyl compound (54 mg, 77% yield) having an R$_f$=0.8 on Si gel in 20% EA/CH$_2$Cl$_2$. The R$_f$ of the starting hydroxymethyl carbapenem in the same system was 0.4.

B4:

A solution of the tris-allylated arylketone (35 mg; 0.04 mmole) in xylene (3 ml) in the presence of a few crystals of hydroquinone was heated at reflux under N$_2$ for 1 hour. The reaction mixture was concentrated in vacuo without heat. The residue was purified by preparative TLC on 1-500μ Si Gel GF plate (eluting with 10% EA/CH$_2$Cl$_2$ and extracting with 10% MeOH/CH$_2$Cl$_2$) to give the tris allyl-protected carbapenem (5.4 mg, 23% yield).

R$_f$(10% EA/CH$_2$Cl$_2$): 0.68.

IR (CH$_2$Cl$_2$): 1780 (β-lactam); 1745 and 1715 (carbonate and ester carbonyls) cm$^{-1}$.

STEP C: DEBLOCK OF CARBINOL, ALDEHYDE, AND CARBOXYLIC ACID Conditions: Pd(Ph$_3$)$_4$; PPh$_3$

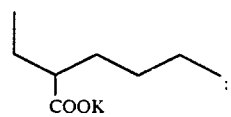

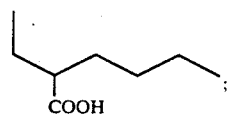

EtOAc:CH$_2$Cl$_2$ (1:1); 2 hrs; ambient temp.

Yield: 47% of carbinol 181

Spectra of 181:

UV (H$_2$O): λmax=267 nm; λsh=305 nm (NH$_2$OH quenchable)

ε: 8,000.

$^1$H NMR (300 MHz, D$_2$O): (no internal standard-DOH at 4.80); δ1.28 (d, J=6 Hz, C$\underline{H}_3$CHO—); 3.02 (dd, J=10 & 18 Hz, H$_{1a}$); 3.39 (dd, J=8 & 18 Hz, H$_{1b}$); 3.44 (dd, J=3 & 6 Hz, H$_6$); 4.15-4.26 (m, H$_5$ and CH$_3$C$\underline{H}$O); 4.79 (s, C$\underline{H}_2$OH); 7.20-7.56 (m's, phenyl and thienyl protons)

Yield: 64% of aldehyde 193

Spectra of 193:

UV (H$_2$O): λmax=260 nm; λsh=300 nm (NH$_2$OH quenchable)

ε: 11,000

$^1$H NMR (300 MHz, D$_2$O): (no internal standard-DOH at 4.80); δ1.27 (d, J=6 Hz, C$\underline{H}_3$CHO); 2.92 (dd, J=10 & 18 Hz, H$_{1a}$); 3.31 (dd, J=8 & 18 Hz, H$_{1b}$); 3.42 (br dd, H$_6$); 4.21 (m, CH$_3$C$\underline{H}$O & H$_5$); 7.19-8.00 (phenyl and thiophene protons); 9.63 (s, CHO)

Yield: 33% of potassium salt 183

For the preparation of 183, the general procedure of deallylation was followed except for the addition of one more equivalent of potassium 2-ethylhexanoate to aid the deblock of the third allyl group.

Spectra of 183:

$^1$H NMR (300 MHz, D$_2$O): (no internal standard-DOH at 4.80); δ1.29 (d, J=6 Hz, C$\underline{H}_3$CHO—); 3.11 (dd, J=10 & 18 Hz, H$_{1a}$); 3.47 (dd, J=8 & 18 Hz, H$_{1b}$); 3.51 (m, H$_6$); 4.22-4.34 (m, CH$_3$C$\underline{H}$O & H$_5$); 7.28-7.86 (m's, phenyl and thiophene protons)

EXAMPLES EMPLOYING STANNANE CHEMISTRY

EXAMPLE 27

Sodium (1'R,5R,6S)-6-(1'-hydroxyethyl)-2-[3''-hydroxymethyl-5''-(thien-2'''-yl)phenyl]carbapen-2-em-carboxylate

STARTING MATERIAL SYNTHESIS:

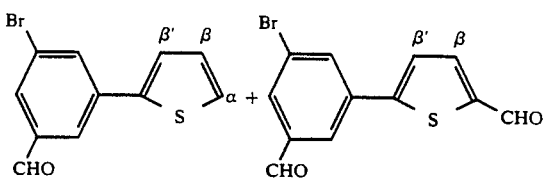

To a solution of 2-(3',5'-dibromophenyl)thiophene (2.86 g, 9 mmol) in THF (30 ml) with stirring at −78° under N$_2$, 1.6M BuLi (5.8 ml, 9.3 mmol) was added dropwise via an addition funnel. After a few mins. for the addition and 5 min. additional stirring, DMF (0.9 ml, 11.6 mmol) was added, and the reaction was allowed to warm to ambient temperature. Stirring was continued for 3 h. The yellow solution was then poured into brine (200 ml) and Et₂O (100 ml), shaken, and separated. The aqueous layer was again extracted with Et₂O, and the combined organic layers were washed with 1:1 brine/H₂O (100 ml), dried (MgSO₄), filtered and concentrated in vacuo to a yellow liquid with a tan precipitate. Hexane (a few ml) was added, and the residue was slurried and filtered. The insoluble portion was washed 2x with hexane (few ml), and the solid dried in vacuo to give the diformylated material (496 mg, 19% yield). The hexane-soluble filtrate was re-concentrated in vacuo (2.38 g) and chromatographed on 60 g of Bakers Si gel (60–200 mesh) packed in hexane. The material was applied to the column in 1:2 CH₂Cl₂/hexane and eluted with the same solvent system (300 ml) after which 10% Et₂O in hexane was used to elute the monoformyl material (814 mg). Approximately 630 mg of the material required further purification on 10-1000μ Si Gel GF plates (eluting and extracting with CH₂Cl₂) to provide the purified monoformylated compound (713 mg, 30% yield)

Data for 2-(3'-bromo-5'-formyl)phenylthiophene: MS: m/z 266/268 (MI)

¹H NMR (300 MHz, CDCl₃): δ7.06 (dd, J=4 and 6 Hz, H$_\beta$); 7.32 (dd, J=0.5 and 6 Hz, H$_\alpha$); 7.33 (dd, J=0.5 and 4 Hz, B$_{\beta'}$); 7.82, 7.90 and 7.96 (3 m's, 3 phenyl H's); 9.93 (s, CHO)

Data for 5-(3'-bromo-5'-formyl)phenyl-2-thiophenecarboxaldehyde: MS: m/z 294/296 (MI)

¹H NMR (300 MHz, CDCl₃): δ7.43 & 7.73 (2 d's, J=4 Hz, H$_\beta$ & H$_{\beta'}$); 7.95, 7.97 and 8.01 (3 m's, 3 phenyl H's); 9.87 & 9.94 (2 s's, 2 CHO's).

2-(3'-BROMO-5'-HYDROXYMETHYL)PHENYL-THIOPHENE:

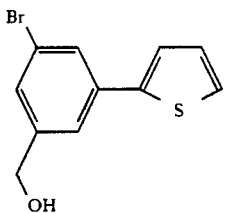

To a solution of 2-(3'-bromo-5'-formyl)thiophene (707 mg, 2.7 mmol) in MeOH (26 ml) with stirring at 0° was added NaBH₄ (125 mg, 3.3 mmol), and after some initial foaming, stirring was continued at 0° for 35 min. The reaction mixture was concentrated to a small volume of yellow oil under a N₂ stream. Et₂O (30 ml) and brine (30 ml) were added, and the reaction mixture was shaken in a separatory funnel. After phase separation, the aqueous layer was again extracted with ether. The combined organic layers were backwashed with brine, dried (MgSO₄), filtered and concentrated in vacuo to give the crude alcohol (735 mg) as an off-white solid. Preparative TLC of 304 mg of this substance on 4-1000μ Si Gel GF plates (eluting with 5% EA/CH₂Cl₂ and extracting with 10% MeOH/CH₂Cl₂) provided the purified hydroxymethyl compound (278 mg).

¹H NMR (300 MHz, CDCl₃): δ4.72 (s, CH₂OH); 7.06 (m, H$_\beta$ of thiophene); 7.30 (m, H$_\alpha$ and H$_{\beta'}$ of thiophene); 7.42, 7.50 & 7.66 (3 br m's, phenyl H's).

2-[3'-(TRIMETHYLTIN)-5'-(HYDROXYMETHYL)PHENYL]THIOPHENE:

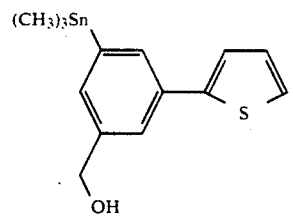

To a solution of the bromohydroxymethyl compound (274 mg, 1.0 mmol) in toluene (4 ml), tetrakistriphenylphosphine palladium (24 mg, 0.02 mmol) and triphenylphosphine (2.9 mg, 0.01 mmol) were added. A gentle stream of N₂ was blown through the reaction mixture followed by the addition of hexamethylditin (459 mg, 1.4 mmol) in toluene (1 ml). The reaction mixture was covered with N₂ and refluxed for 2 h. By analytical TLC the reaction appeared to stop at a 50% conversion, so additional tetrakistriphenylphosphine palladium (22 mg) was added, and heating was continued for another hour whereupon analytical TLC indicated essentially 100% conversion to a less polar spot (5% EA/CH₂Cl₂). The reaction mixture was partitioned between EA/H₂O and cold saturated NaHCO₃. The organic layer was then washed 3x cold saturated NaHCO₃, 2x brine, dried (MgSO₄), filtered, and concentrated in vacuo to a yellow oil. Preparative TLC on 4-1000μ Si Gel GF plates (eluting with 5% EA/CH₂Cl₂ and extracting with CH₂Cl₂) provided the purified trimethyltin compound (246 mg, 69% yield).

¹H NMR (300 MHz, CDCl₃): δ0.33 (m, (CH₃)₃Sn); 1.72 (t, J=6 Hz, OH); 4.73 (d, J=6 Hz, CH₂OH); 7.10 (m, H$_\beta$ of thiophene), 7.30 (2-m's, H$_\alpha$ and H$_{\beta'}$ of thiophene); 7.40, 7.55 & 7.63 (3-br m's, phenyl H's).

STANNANE COUPLING TO PREPARE CARBAPENEMS:

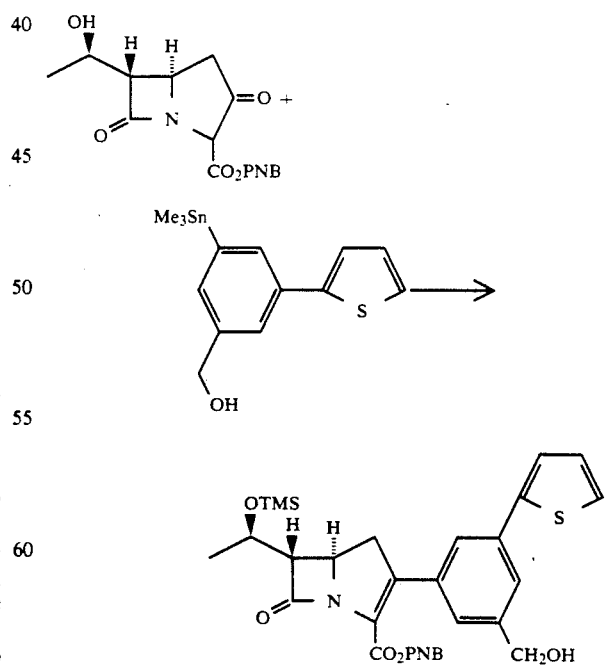

In a 2-neck 25 ml round-bottom flask, a solution of the β-keto ester pictured above (obtained as in Flow Sheet B2) (109 mg, 0.31 mmol) in anhydrous THF (1.5 ml) was purged with $N_2$. With stirring, the solution was cooled to $-78°$, and diisopropylamine (48 μl, 0.34 mmol) was added dropwise via a syringe. After 10 minutes, triflic anhydride (57 μl, 0.32 mmol) was added dropwise via syringe. After 15 min. triethylamine (47 μl, 0.34 mmol) was added followed by trimethylsilyltriflate (66 μl, 0.34 mmol), and stirring was continued for 20 min. A solution of the trimethyltin compound (118 mg, 0.34 mmol) in N-methyl-3-pyrrolidinone followed by a mixture of tris (2,4,6-trimethoxyphenyl)phosphine (13.5 mg, 0.025 mmol) and $Pd_2(DBA)_3 \cdot CHCl_3$ (7.6 mg; 0.007 mmol) were added followed immediately by 1.5M $ZnCl_2$ in $Et_2O$ (277 μl, 0.34 mmol). The $-78°$ bath was removed, and the reaction mixture was quickly brought to ambient temperature in a luke-warm water bath. The burgundy-colored solution was stirred for 30 min. and then poured into $Et_2O$ (60 ml)/EA (15 ml)/$H_2O$ (11 ml). After shaking well and separation of phases, the organic layer was washed 3x with 1:1 brine/$H_2O$ (15 ml), dried ($MgSO_4$ and treated with 30 mg charcoal), filtered and concentrated in vacuo to give a pink foam, the crude product (238 mg). Chromatography on a small column of Bakers Si Gel (60-200 mesh), packed and applied in $CH_2Cl_2$ and eluting with $CH_2Cl_2$ (20 ml), 5% $EA/CH_2Cl_2$ (100 ml), 10% $EA/CH_2Cl_2$, etc. provided the purified carbapenem (106 mg. 58% yield).

MS: m/z 592 (MI); 434 (MI-β-lactam cleavage); 117 ($CH_3CHOTMS$), 73 (TMS)

IR($CH_2Cl_2$): 1775 (β-lactam); 1722 (ester) cm$^{-1}$ $^1$H NMR (300 MHz, $CDCl_3$): δ0.14 (s, TMS); 1.29 (d, J=6 Hz, $CH_3CHO$—); 1.76 (t, J=6 Hz, OH); 3.22 (dd, J=10 & 18 Hz, $H_{1a}$); 3.25 (dd, J=3 and 6 Hz, $H_6$); 3.33 (dd, J=8 & 18 Hz, $H_{1b}$); 4.20–4.31 (m's, $CH_3CHO$ & $H_5$); 4.69 (d, J=6 Hz, $CH_2OH$); 5.25 (midpt. of 2d, J=14 Hz, non equivalent $\overline{CO_2CH_2}Ar$): 7.04 (m, 4'''-H of thiophene); 7.27 (m, 2-thiophene H's & 1-phenyl H); 7.41 and 8.07 (2 d's, J=9 Hz, $ArpNO_2$); 7.46 & 7.54 (2-br s's phenyl H's).

DEBLOCK (HYDROLYSIS OF SILYL ETHER AND HYDROGENOLYSIS OF p-NITROBENZYLESTER):

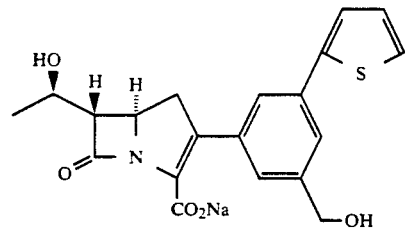

A solution of the protected carbapenem (100 mg, 0.17 mmol) in THF (3.9 ml), EtOH (3.9 ml) and $H_2O$ (3 ml) was treated with HOAc (3 μl, 0.05 mmol). The clear, colorless solution was stirred under $N_2$ for 3 hrs. at 35°. After cooling to ambient temperature, the desilylated reaction mixture was briefly stirred with $NaHCO_3$ (31 mg, 0.37 mmol). The reaction mixture was covered with $N_2$, 10% Pd/C (13 mg) was added, and the reaction mixture was placed under a $H_2$-filled balloon and stirred for 1 hr at ambient temperature. After filtering through a pad of celite and washing the pad well with additional water, the yellow filtrate clouded and solids precipitated. Upon transfer of this filtrate to centrifuge tubes and extraction with EtOAc, phase separation was still difficult due to emulsions. The aqueous layer was separated and lyophilized at 0° to provide 60 mg yellow lyophilizate. The 60 mg was treated with 12% MeCN/$H_2O$ (1.5 ml), stirred well, and then centrifuged, after which the yellow aqueous layer was purified by preparative TLC on 3-1000μ RPS-F plates (eluting with 12% MeCN/$H_2O$ in the cold and extracting the main UV active band with 4:1 MeCN/$H_2O$ 60 ml). The usual work-up of the plates and lyophilization provided the purified title compound (19 mg, 28%).

UV($H_2O$): λmax=290 nm, ε=19,000

$^1$H NMR (300 MHz, $D_2O$): (no internal standard-DOH at 4.80) δ1.27 (d, J=6 Hz, $CH_3CHOH$—); 2.94 (dd, J=10 & 18 Hz, $H_{1a}$); 3.33 (dd, J=8 & 18 Hz, $H_{1b}$); 3.43 (dd, J=3 & 6 Hz, $H_6$); 4.18–4.24 (m's, $H_{1'}$ & $H_5$); 4.57 (s, $CH_2OH$); 7.11 (m, 4'''-thiophene H); 7.39–7.46 (m's, 2-thiophene H's & 3-phenyl H's).

EXAMPLE 29

Sodium (1'R,5R, 6S)-6-(1'-hydroxyethyl)-2-(3''-formyl-5''-thien-2'''-yl)phenyl]-carbapen-2-em carboxylate

STARTING MATERIAL SYNTHESIS:
2-[3'-(TRIMETHYLTIN)-5'-(FORMYL)-PHENYL]THIOPHENE:

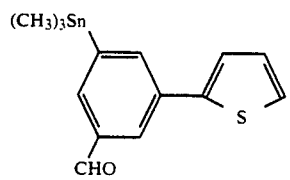

A solution of 2-[3'-(trimethyltin)-5'-(hydroxymethyl)-phenyl]thiophene (118 mg, 0.34 mmol) was re-oxidized in benzene (10 ml) in the presence of $MnO_2$ (1g, excess). The reaction mixture was stirred vigorously for 24 hrs. The next day the reaction was filtered, and the insolubles rinsed repeatedly with $CH_2Cl_2$. The combined filtrates were concentrated in vacuo, then redissolved in $CH_2Cl_2$, dried ($MgSO_4$), filtered and concentrated as above to give the crude product. Preparative TLC on 2-1000μ Si Gel GF plates (eluting with 1:1 hexane:$CH_2Cl_2$ and extracting with $CH_2Cl_2$) provided the purified formyl compound (84 mg, 71%).

IR ($CH_2Cl_2$): 1695 (CHO)cm$^{-1}$:

$^1$H NMR (300 MHz, $CDCl_3$): 0.38 (m, $(CH_3)_3Sn$); 7.11 (m, 4'''-thiophene H); 7.35 & 7.39 (2-m's, 2-thiophene H's): 7.89, 7.94 & 8.00 (3-m's, 3-phenyl H's); 10.04 (s, CHO).

STANNANE COUPLING:

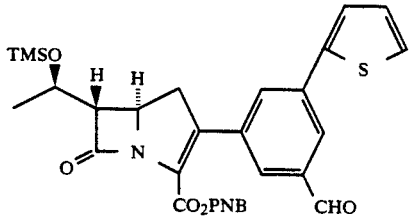

A solution of the β-ketoester (79 mg, 0.23 mmol) was treated as indicated in Example 27, Stannane Coupling, using a solution of the formyl compound (84 mg, 0.24 mmol) to provide upon work-up the crude carbapenem (134 mg), a pink foam. Chromatography on a small column of Bakers Si Gel (60-200 mesh) packed and applied in CH₂Cl₂ and eluted with CH₂Cl₂ until the pink band had emerged was followed by elution with 1% EtOAc/CH₂Cl₂. The appropriate fractions were dried (MgSO₄) and concentrated to provide the purified carbapenem (79 mg; 58%).

MS: m/z 590(MI); 432 (β-lactam cleavage); 117(CH₃CHOTMS); 73 (TMS).

IR (CH₂Cl₂): 1780 (β-lactam); 1725 (ester carbonyl); 1700 (formyl)cm⁻¹;

¹H NMR (300 MHz, CDCL₃): δ0.15 (s, TMS); 1.30 (d, J=6 Hz, CH₃CHOTMS); 3.27(dd, J=10 & 18 Hz, H₁ₐ); 3.30 (dd, J=3 & 6 Hz, H₆); 3.39 (dd, J=8 & 18 Hz, H₁ᵦ); 4.22–4.36 (m's, H₁' & H₅); 5.27 (midpt. of 2d, J=14 Hz, non-eq. CO₂CH₂Ar); 7.09 (m, 4'''-thiophene H); 7.34 (m, 2-thiophene H's); 7.46 & 8.09 (2d's, J=8 Hz, ArpNO₂); 7.72, 7.80 & 8.01 (3-m's, 3-phenyl H's); 10.00 (s, CHO).

DEBLOCK:

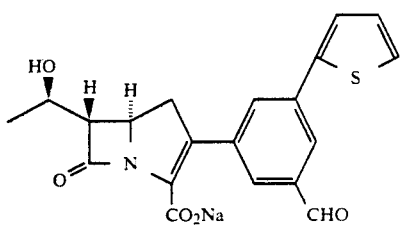

A solution of the carbapenem (77 mg, 0.13 mmol) was deblocked as was the analogous hydroxymethyl carbapenem in Example 27, except that an increased amount of catalyst, 10% Pd/C (22 mg) was used. After 30 min under a balloon filled with H₂, another 22 mg of 10% Pd/C was introduced, and the hydrogenolysis was continued for 30 min more. The solution was transferred to a centrifuge test tube, and most of the catalyst was centrifuged to the bottom. The supernatant was placed in a flask, and the catalyst was washed 4× with H₂O (5 ml) filtering into the original flask through a pad of celite. The clear filtrate was concentrated to a small volume with little or no heat in vacuo and then lyophilized at 0° to give the crude product (69 mg). The crude material was applied in 1.2 ml H₂O to 2-1000μ RPS-F plates eluting with 30% CH₃CN/H₂O in the cold to give upon the usual work-up and lyophilization a sample of the title compound (23 mg) which contained an impurity by 300 MHz ¹H-NMR. Further purification on 2-1000μ RPS-F plates eluting with 15% CH₃CN/H₂O provided separation of the desired product from a forward running impurity, suspected to be the analogous carbapenam resulting from double bond reduction. The usual work-up of the plates and lyophilization provided the title compound (12 mg, 23% yield) free of the impurity.

UV(H₂O): λₘₐₓ=290 mμ, ε=8,900

¹H-NMR (300 MHz, D₂O): 1.32 (d, J=6 Hz, CH₃CHOH—); 2.98 (dd, J=10 & 16 Hz, H₁ₐ); 3.34 (dd, J=8 & 16 Hz, H₁ᵦ); 3.48 (dd, J=3 & 6 Hz, H₆); 4.20–4.30 (m's H₁' & H₅); 7.12 (m, 4'''-thiophene H); 7.38 & 7.44 (2-m's, 2 thiophene H's); 7.58, 7.68 & 7.78 (3 br s's, phenyl H's); 9.70 (s, formyl).

EXAMPLE 76

Sodium (1'R, 5R, 6S)-6-(1'-hydroxyethyl)-2-[3''-hydroxymethyl-5''-(2'''-hydroxymethylthien-5'''-yl)-phenyl]-carbapen-2-em-carboxylate STARTING MATERIAL SYNTHESIS:
5-(3'-BROMO-5'-HYDROXYMETHYL)PHENYL-2-HYDROXYMETHYLTHIOPHENE:

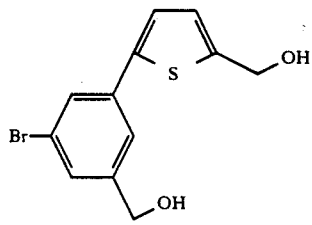

A sample of 5-(3'-bromo-5'-formyl)phenyl-2-thiophenecarboxaldehyde from Example 27, (223 mg, 0.76 mmol) was dissolved in MeOH (15 ml) and cooled to 0° with stirring. To the still partially heterogeneous reaction mixture NaBH₄ (73 mg, 1.9 mmol) was added. After 1 hour at 0° during which time a homogeneous solution had resulted, the solution was concentrated under a N₂ stream. Partitioning between brine (20 ml)/Et₂O (20 ml)/and EA (10 ml), the phases were separated, and the aqueous layer again extracted with EA. The combined organic layers were washed with brine, dried (MgSO₄), filtered, and concentrated in vacuo to give the crude product. Preparative TLC on 4-1000μ Si Gel GF plates (applied in warm acetone, eluted and extracted with 10% MeOH/CH₂Cl₂) provided the purified diol (161 mg, 71% yield).

¹H NMR (300 MHz, d₆DMSO); δ4.52 (d, J=6 Hz, CH₂OH); 4.63 (d, J=6 Hz, CH₂OH); 5.40 (t, J=6 Hz, CH₂OH); 5.65 (t, J=6 Hz, CH₂OH); 6.96 & 7.43 (2 d's, J=4 Hz, thiophene H's) 7.40, 7.52 & 7.68 (3 br s's, 3 phenyl H's)

5-(5'-HYDROXYMETHYL-3'-TRIMETHYLTIN)PHENYL-2-HYDROXYMETHYLTHIOPHENE:

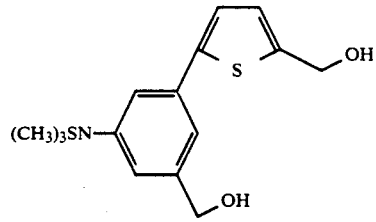

The diol (161 mg, 0.54 mmol) was treated as the monohydroxymethyl compound had been treated in Example 27, using hexamethylditin (200 μl, 0.9 mmol). After 1 hour at reflux, the reaction appeared by analytical TLC to have progressed only very slightly. An additional 19 mg of tetrakistriphenylphosphine palladium was added, and refluxing was continued for 1 hour. More catalyst (26 mg) was added, and after another hour at reflux the conversion was fairly complete. Work-up as in Example 27 provided the crude product (303 mg). Extensive preparative TLC chromatography eluting with 10% MeOH/CH₂Cl₂, isolating, then eluting with 50% EA/hexane, isolating, and then eluting with 5% MeOH/CH$_2$Cl$_2$ finally provided the purified trimethyltin compound (92 mg, 45% yield)

$^1$H NMR (300 MHz, CDCl$_3$): δ0.32 (m, (CH$_3$)$_3$Sn); 1.68 (t, J=6 Hz, OH); 1.79 (t, J=6 Hz, OH); 4.72 (d, J=6 Hz, CH$_2$OH); 4.83 (d, J=6 Hz, CH$_2$OH); 6.97 & 7.18 (2 d's, J=4 Hz, thiophene H's); 7.40 7.52 & 7.60 (3 m's, 3 phenyl H's).

STANNANE COUPLING AND DESILYLATION:

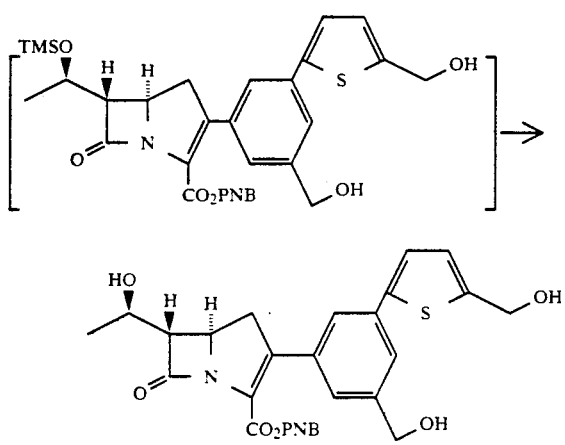

A solution of the β-ketoester (75 mg, 0.22 mmol) was treated as indicated in Example 27, Stannane Coupling, using a solution of diol (90 mg, 0.24 mmol) to provide upon work-up the crude carbapenem (104 mg). Since the crude material appeared to be partially desilylating on Si Gel, it was immediately treated with THF (5.5 ml), EtOH (5.5 ml), H$_2$O (4.2 ml), HOAc (4.2 μl) with stirring under N$_2$ at 35° for 1 hour to give the more polar, desilylated carbapenem. The reaction mixture was concentrated a bit under N$_2$ and then stirred well with 1M K$_2$HPO$_4$ (1 ml), H$_2$O and EA. After phase separation, the organic layer was extracted with a combination of 1M K$_2$HPO$_4$(1 ml)/H$_2$O/brine. The organic layer was dried (Na$_2$SO$_4$) and concentrated in vacuo. Preparative TLC (applied and eluted in 8% MeOH/CH$_2$Cl$_2$ and extracted with 10% MeOH/CH$_2$Cl$_2$) provided the purified desilylated carbapenem (68 mg, 64% yield) ready for hydrogenolysis.

DEBLOCK:

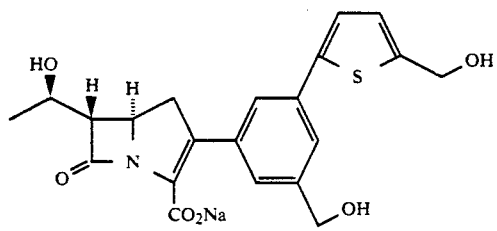

To a stirred solution of the desilylated carbapenem (68 mg, 0.12 mmol) in THF (2.9 ml), EtOH (2.9 ml) and H$_2$O (2.2 ml) was added NaHCO$_3$ (14 mg, 0.17 mmol) followed by 10% Pd/C (29 mg), and the reaction was covered with a balloon of H$_2$ for 30 min. An additional 30 mg of catalyst was added, and the hydrogenolysis was continued as above for another hr. The usual work-up and lyophilization provided the crude product which was purified by preprative TLC on 2-1000μ RPS-F plates eluting in the cold with 15% CH$_3$CN/H$_2$O. The usual work-up of the plates and lyophilization provided the purified title compound (24 mg, 46% yield).

UV(H$_2$O): λ$_{max}$=295 mμ; ε=20,000.

$^1$H NMR (300 MHz, D$_2$O): δ1.26 (d, J=6 Hz, CH$_3$CHOH—), 2.94 (dd, J=10 & 17 Hz, H$_{1a}$); 3.31 (dd, J=8 & 17 Hz, H$_{1b}$); 3.42 (dd, J=2 & 3 Hz, H6); 4.2 (m, H$_1$' & H$_5$); 4.54 & 4.72 (2 s's, 2 CH$_2$OH's); 6.99 & 7.22 (2 d's, J=4 Hz, thiophene H's); 7.14, 7.40 & 7.43 (3 br s's, phenyl H's).

EXAMPLE 78

Sodium (1'R, 5R, 6S)-6-(1'-hydroxyethyl)-2-[3''-formyl-5''-(2'''-formylthien-5'''-yl)phenyl]carbapen-2-em-carboxylate

STARTING MATERIAL SYNTHESIS:

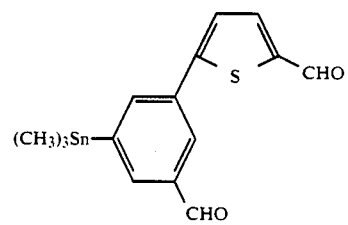

The 5-(3'-bromo-5'-formyl)phenyl-2-thiophenecarboxaldehyde from Example 27 (225 mg, 0.77 mmol) was stannylated as the hydroxymethyl compound had been in Example 27. After 1.5 h at reflux, additional catalyst (21 mg) and a total of 485 mg hexamethylditin (1.5 mmol) was added. After refluxing for an additional 2 hours, the conversion was judged complete by analytical TLC, and the reaction mixture was refrigerated overnight. Work-up as in Example 27 provided the crude product (340 mg). Preparative TLC on 4-1000μ Si Gel GF plates (eluting with 30% EA/Hexane and extracting with 10% MeOH/CH$_2$Cl$_2$) provided the purified trimethyltin compound (159 mg, 54% yield).

IR(CH$_2$Cl$_2$): 1700 and 1670 (formyls) cm$^{-1}$ $^1$H NMR (300 MHz, CDCl$_3$); δ0.37 (m, (CH$_3$)$_3$Sn); 7.03 & 7.30 (2 d's, J=4 Hz, thiophene H's); 7.50 & 7.59 (2, m's, phenyl H's); 9.31 & 9.46 (2 s's, 2 CHO's).

STANNANE COUPLING:

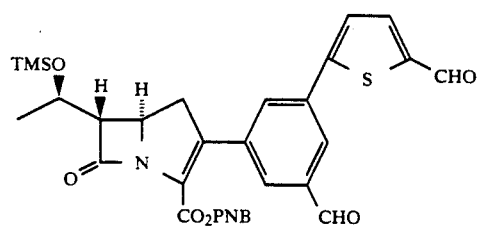

A solution of the β-ketoester (133 mg 0.38 mmol) was treated as indicated in Example 27, Stannane Coupling, using a solution of the dialdehyde (155 mg, 0.41 mmol) to provide upon work-up the crude carbapenem (221 mg). Chromatogaphy on a small column of Bakers Si Gel (60-200 mesh) eluting with CH$_2$Cl$_2$ until the red band was halfway down the column and then switching to 5% EA/CH$_2$Cl$_2$ provided the purified carbapenem (115 mg, 49%).

MS: m/z 618(MI) 460 (β-lactam cleavage), 117 (CH₃CHOTMS), 73 (TMS)

IR(CH₂Cl₂) 1780 (β-lactam), 1725 (ester), 1700 and 1670 (formyls) cm⁻¹

¹H NMR (300 MHz, CDCl₃): δ0.16 (d, J=6 Hz, CH₃CHOTMS); 3.27 (dd, J=10 & 18 Hz, H$_{1a}$); 3.30 (dd, J=2.5 & 6 Hz, H₆); 3.40 (dd, J=9 & 18 Hz, H$_{1b}$); 4.24–4.38 (m's, H$_{1'}$ & H₅); 5.30 (midpt. of 2 d, J=14 Hz, non-equivalent CO₂C$\overline{H}$₂Ar); 7.44 & 7.76 (2 d's, J=4 Hz, 2 thiophene H's); 7.55 & 8.14 (2 d's, J=9 Hz, ArpNO₂); 7.85, 7.93 & 8.08 (3 m's, 3 phenyl H's); 9.92 & 10.04 (2 s's, 2 CHO's).

DEBLOCK:

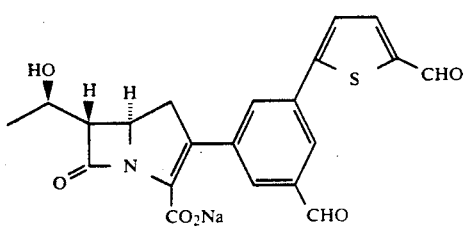

A solution of the carbapenem (110 mg, 0.18 mmol) was deblocked as was the carbapenem in Example 27, Deblock. Upon work-up severe clogging of the celite pad resulted. The celite was washed with a THF/EtOH/H₂O mixture, and all filtrates were concentrated in vacuo with little or no heat and then lyophilized at 0° to a yellow solid. Water (2 ml) was added to produce a slurry which was extracted 2× with EA (2 ml), and the aqueous layer was then purified by preparative TLC on 3-1000μ RPS-F plates eluting with 10% MeCN/H₂O in the cold. The usual work-up of the plates and lyophilization provided a low yield of the pure title compound (4 mg, 5%).

UV(H₂O): λ$_{max}$=328 nm, ε=23,000

¹H NMR (300 MHz, D₂O): δ1.35 (d, J=6 Hz, CH₃CHOH—); 3.09 (dd, J=10 & 16 Hz, H$_{1a}$); 3.44 (dd, J=8 & 16 Hz, H$_{1b}$); 3.54 (dd, J=3 & 6 Hz, H₆); 4.26–4.37 (m's, H$_{1'}$ & H₅); 7.49 & 7.90 (2 d's J=4 Hz, 2 thiopene H's); 7.76, 7.79 and 7.90 (3 m's, 3 phenyl H's); 9.74 & 9.81 (2 s's, CHO's).

EXAMPLE 185

Sodium (1'R,5R,6S)-6-(1'-hydroxyethyl)-2-[(3''-carbamyl-5''-thien-2'''-yl)phenyl]carbapen-2-em-carboxyxlate

STARTING MATERIAL SYNTHESIS:
3-BROMO-5-(THIEN-2'-YL)BENZOIC ACID:

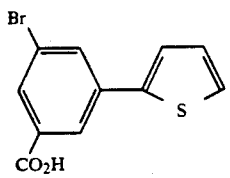

To a solution of 2-(3'-bromo-5'-formyl)phenylthiophene (100 mg, 0.38 mmol) from Example 27 in acetone (3.9 ml) with stirring at 0°, Jones reagent (85 μl, 2.6M in CrO₃, 0.22 mmol) was added. After 30 min some aldehyde was still present by TLC. An additional 85 μl Jones reagent was added and stirring continued at 0° for 30 min. Isopropanol (73 μl) was added to quench any excess oxidant, and after 5 min at 0°, the reaction mixture was concentrated under a N₂ stream. The green residue was partitioned between EA and H₂O. The aqueous phase was again extracted with EA, and the combined organic layers were washed with brine, dried (MgSO₄), filtered, and concentrated in vacuo. The residue was dissolved in EA and H₂O to which was added 5 N NaOH (152 μl, 0.76 mmol), and the layers were shaken well. The light brown aqueous layer was extracted 2x with EA and then layered with a third fresh quantity of EA. After addition of 2N HCl (380 μl, 0.76 mmol) and vigorous shaking, the organic layer was separated and the aqueous layer again extracted with EA. The combined organic layers were washed with brine, dried (MgSO₄), filtered, and concentrated in vacuo to provide the purified carboxylic acid (84 mg, 79%).

3-BROMO-5-(THIEN-2'-YL)BENZAMIDE:

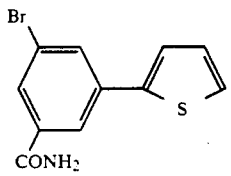

To a solution of the carboxylic acid (84 mg, 0.3 mmol) in CH₃CN (4.3 ml) with stirring was added 1-(3-dimethylaminopropyl)-3-ethylcarbodiimide hydrochloride (75 mg, 0.39 mmol) and 1-hydroxy benzotriazole hydrate (78 mg, 0.58 mmol) dissolved in THF (4.3 ml). The solution was stirred under N₂ for 20 min, and then a solution of 2.3M NH₃ in ethanol (3.4 ml, 7.8 mmol) was added causing the previously clear reaction to turn cloudy. After stirring at room temperature for 20 min, the reaction was concentrated under a N₂ stream and then in vacuo. The residue was partitioned between EA and H₂O, shaken well, the phases separated, and the aqueous was again extracted with EA. The combined organic layers were washed with brine, dried (MgSO₄), filtered and concentrated in vacuo to give the crude amide (95 mg) as a tan solid. The material was dissolved in THF and chromatographed on 2-1000μ Si Gel GF plates (eluting with 5% MeOH/CH₂Cl₂ and extracting with 10% MeOH/CH₂Cl₂) to provide the purified amide (69 mg, 82% yield). MS: m/z 281/283 (MI).

¹H-NMR (300 MHz, acetone-d₆): δ6.85 (br abs, one NH of amide); 7.20, 7.58 and 7.56 (3 m's, 3 thiophene H's); 7.76 (br abs, 2$^{nd}$ NH of amide); 8.00 & 8.20 (br m's, 3 phenyl H's).

3-(TRIMETHYLTIN)-5-(THIEN-2'-YL)BENZAMIDE:

The benzamide (67 mg, 0.24 mmol) was treated as the analogous hydroxymethyl compound had been treated in Example 27. After 1 hour at reflux, a second batch of both the Pd° and phosphine catalysts was added, and refluxing was continued until conversion to the faster running product was completed. Work-up as in Example 27 provided the crude product (101 mg). This material was partially purified by preparative TLC on 2-1000μ Si Gel GF plates (eluting and extracting with 10% MeOH/CH$_2$Cl$_2$). A second preparative TLC (eluting with 50% EA/hexane and extracting with 50% EA/CH$_2$Cl$_2$) provided the purified trimethyltin compound (59 mg, 67% yield). MS: m/z 367(MI); 352(MI-CH$_3$)

IR(CH$_2$Cl$_2$): 1680 (amide) cm$^{-1}$ $^1$H NMR (300 MHz, CDCl$_3$): δ0.35 (m, (CH$_3$)$_3$Sn); 6.05 & 6.20 (2 humps, CONH$_2$'s); 7.09 (m, 4'''-thiophene H); 7.32 & 7.36 (2 m's, 2 thiophene H's); 7.81, 7.83 and 7.95 (3 m's, 3 phenyl H's).

STANNANE COUPLING:

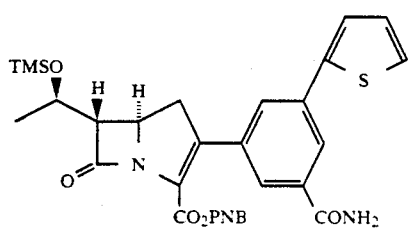

A solution of the β-ketoester (53 mg, 0.15 mmol) was treated as indicated in Example 27, Stannane Coupling, using a solution of the amide (57 mg, 0.16 mmol), to provide upon work-up the crude carbapenem (88 mg). Chromatography on a small column of Bakers Si Gel (60-200 mesh) eluting with CH$_2$Cl$_2$ (50 ml) then 20% EA/CH$_2$Cl$_2$ provided the purified carbapenem (57 mg, 63% yield).

IR(CH$_2$Cl$_2$): 1780 (β-lactam), 1725 (ester), 1685 (amide) cm$^{-1}$ $^1$H NMR (300 MHz, CDCl$_3$): δ0.16 (s, TMS); 1.31 (d, J=6 Hz, CH$_3$CHOTMS—); 3.22-3.41 (3 dd, H$_{1a}$, H$_{1b}$ & H$_6$); 4.22-4.32 (m, H$_{1'}$ & H$_5$); 5.27 (midpt. of 2d's J=14 Hz, non-eq. CO$_2$CH$_2$Ar); 5.63 & 6.10 (2 humps, CONH$_2$); 7.08 (m, 4'''-thiophene H); 7.33 (2 m's, 2 thiophene H's); 7.46 & 8.10 (2d's, J=9 Hz, ArpNO$_2$); 7.49, 7.54 & 7.93 (3 m's, 3 phenyl H's).

DEBLOCK:

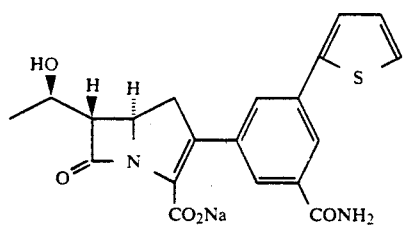

A solution of the carbapenem (55 mg, 0.09 mmol) was deblocked as was the carbapenem in Example 29, Deblock. After the usual desilylation, 10% Pd/C (27 mg) was added, and the reaction mixture was stirred under a balloon of H$_2$ for 30 min. An additional 28 mg of 10% Pd/C was added and the hydrogenolysis continued for an additional hour. After work-up as described in Example 29, the lyophilizate was purified by preparative TLC on 2-1000μ RPS-F plates eluting with 15% MeCN/H$_2$O in the cold to give upon the usual work-up and lyophilization a sample of the title compound (21 mg) which contained a minor amount of what appeared to be a double bond reduced analog by 300 MHz $^1$H NMR. The material was re-prepped on 2-500μ RPS-F plates eluting with 7% MeCN/H$_2$O, and the UV band was arbitrarily split in half. After the usual work-up and lyophilization, the slower half of the band (4.4 mg) was shown by $^1$H NMR to contain less of the impurity than the faster running half (7.5 mg).

UV(H$_2$O): λ$_{max}$=290 nm; ε=14,000

$^1$H NMR (300 MHz, D$_2$O): δ1.28 (d, J=6 Hz, CH$_3$CHOH—); 3.01 (dd, J=10 & 16 Hz, H$_{1a}$); 3.38 (dd, J=8 and 16 Hz, H$_{1b}$); 3.47 (m, H$_6$); 4.24 (m, H$_{1'}$ & H$_5$); 7.12, 7.38 & 7.42 (3 m's, 3 thiophene H's); 7.50, 7.66 & 7.80 (3 br s's, 3 phenyl H's).

What is claimed is:

1. A compound of the formula:

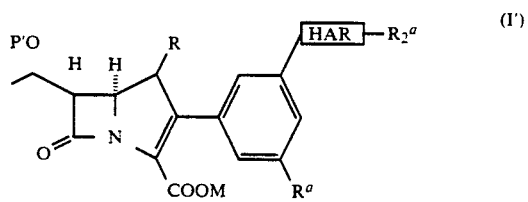

(I')

wherein:

P' is a removable protecting group for hydroxy;

R is H or CH$_3$;

R$^1$ and R$^2$ are independently H, CH$_3$—, CH$_3$CH$_2$—, (CH$_3$)$_2$CH—, HOCH$_2$—, CH$_3$CH(OH)—, (CH$_3$)$_2$C(OH)—, FCH$_2$CH(OH)—, F$_2$CHCH(OH)—, F$_3$CCH(OH)—, CH$_3$CH(F)—, CH$_3$CF$_2$—, or (CH$_3$)$_2$C(F)—;

HAR is a 5- or 9-membered mono- or bicyclic heteroaryl ring system wherein 1 atom is O or S, or an 8-membered bicyclic heteroaryl ring system wherein 2 atoms are O and/or S; all the other atoms being carbon R$^a$ is each independently selected from the group consisting of hydrogen and the radicals set out below:

a) a trifluoromethyl group: —CF$_3$;

b) a halogen atom: —Br, —Cl, —F, or —I;

c) C$_1$-C$_4$ alkoxy radical: —OC$_{1-4}$ alkyl, wherein the alkyl is optionally mono-substituted by R$^q$, where R$^q$ is a member selected from the group consisting of —OH, —OP', —OCH$_3$, —CN, —C(O)NH$_2$, —OC(O)NH$_2$, CHO, —OC(O)N(CH$_3$)$_2$, —SO$_2$NH$_2$, —SO$_2$N(CH$_3$)$_2$, —SOCH$_3$, —SO$_2$CH$_3$, —F, —CF$_3$, —COOM$^a$ (where M$^a$ is hydrogen, alkali metal, methyl, phenyl, or M), tetrazolyl (where the point of attachment is the carbon atom of the tetrazole ring and one of the nitrogen atoms is mono-substituted by M$^a$ as defined above) and —SO$_3$M$^b$ (where M$^b$ is hydrogen, an alkali metal, or M);

d) a hydroxy group: —OH or a protected hydroxy group: —OP';

e) a carbonyloxy radical: —O(C=O)R$^s$, where R$^s$ is C$_1$-C$_4$ alkyl or phenyl, each of which is optionally mono-substituted by R$^q$ as defined above or tri-substituted with —F;

f) a carbamoyloxy radical: —O(C=O)N(R$^y$)R$^z$, where R$^y$ and R$^z$ are independently H, C$_{1-4}$ alkyl (optionally mono-substituted by R$^q$ as defined above), together a 3- to 5-membered alkylidene radical to form a ring (optionally substituted with R$^q$ as defined above) or together a 2- to 4-membered alkylidene radical, interrupted by —O—, —S—, —S(O)—, —S(O)$_2$— or —NR$^e$—, to form a ring (where R$^e$ is hydrogen, C$_1$-C$_4$ alkyl, and C$_1$-C$_4$ alkyl mono-substituted with R$^q$ and the ring is optionally mono-substituted with Rq as defined above);

g) a sulfur radical: —S(O)$_n$—R$^s$ where n=0-2, and R$^s$ is defined above;

h) a sulfamoyl group: —SO$_2$N(R$^y$)R$^z$ where R$^y$ and R$^z$ are as defined above;

i) azido: N$_3$ j) a formamido group: —N(R$^f$)—C(O)H, where R$^f$ is H or C$_1$-C$_4$ alkyl, and the alkyl thereof is optionally mono-substituted by R$^q$ as defined above;

k) a (C$_1$-C$_4$ alkyl)carbonylamino radical: —N(R$^f$)—C(O)C$_{1-4}$ alkyl, where R$^f$ is as defined above, and the alkyl group is also optionally mono-substituted by R$^q$ as defined above;

l) a (C$_1$-C$_4$ alkoxy)carbonylamino radical: —N(R$^f$)—C(O)OC$_1$-C$_4$ alkyl, where R$^f$ is as defined above, and the alkyl group is also optionally mono-substituted by R$^q$ as defined above;

m) a ureido group: —N(R$^f$)—C(O)N(R$^y$)R$^z$ where R$^f$, R$^y$ and R$^z$ are as defined above;

n) a sulfonamido group: —N(R$^f$)SO$_2$R$^s$, where R$^s$ and R$^f$ are as defined above;

o) a cyano group: —CN;

p) a formyl or acetalized formyl radical: —C(O)H or —C(OCH$_3$)$_2$H;

q) (C$_1$-C$_4$ alkyl)carbonyl radical wherein the carbonyl is acetalized; —C(OCH$_3$)$_2$C$_1$-C$_4$ alkyl, where the alkyl is optionally mono-substituted by R$^q$ as defined above;

r) carbonyl radical: —C(O)R$^s$, where R$^s$ is as defined above;

s) a hydroximinomethyl radical in which the oxygen or carbon atom is optionally substituted by a C$_1$-C$_4$ alkyl group: —C(R$^y$)=NOR$^z$ where R$^y$ and R$^z$ are as defined above, except they may not be joined together to form a ring;

t) a (C$_1$-C$_4$ alkoxy)carbonyl radical: —C(O)OC$_{1-4}$ alkyl, where the alkyl is optionally mono-substituted by R$^q$ as defined above;

u) a carbamoyl radical: —C(O)N(R$^y$)R$^z$ where R$^y$ and R$^z$ are as defined above;

v) an N-hydroxycarbamoyl or N(C$_1$-C$_4$ alkoxy)carbamoyl radical in which the nitrogen atom may be additionally substituted by a C$_1$-C$_4$ alkyl group: —(C=O)—N(OR$^y$)R$^z$ where R$^y$ and R$^z$ are as defined above, except they may not be joined together to form a ring;

w) a thiocarbamoyl group: —C(S)N(R$^y$)(R$^z$) where R$^y$ and R$^z$ are as defined above;

x) carboxyl: —COOM$^b$, where M$^b$ is as defined above;

y) thiocyanate: —SCN;

z) trifluoromethylthio:—SCF$_3$;

aa) tetrazolyl, where the point of attachment is the carbon atom of the tetrazole ring and one of the nitrogen atoms is mono-substituted by hydrogen, an alkali metal or a C$_1$-C$_4$ alkyl optionally substituted by R$^q$ as defined above;

ab) an anionic function selected from the group consisting of: phosphono [P=O(OM$^b$)$_2$]; alkylphosphono {P=O(OM$^b$)-[O(C$_1$-C$_4$ alkyl)]}; alkylphosphinyl [P=O(OM$^b$)-(C$_1$-C$_4$ alkyl)]; phosphoramido [P=O(OM$^b$)N(R$^y$)R$^z$ and P=O(OM$^b$)NHR$^x$]; sulfino (SO$_2$M$^b$); sulfo (SO$_3$M$^b$); acylsulfonamides selected from the structures CONM$^b$SO$_2$R$^x$, CONM$^b$SO$_2$N(R$^y$)R$^z$, SO$_2$NM$^b$CON(R$^y$)R$^z$; and SO$_2$NM$^b$CN, where R$^x$ is phenyl or heteroaryl, where heteroaryl is a monocyclic aromatic hydrocarbon group having 5 to 6 ring atoms, in which a carbon atom is the point of attachment, in which one of the carbon atoms has been replaced by a nitrogen atom, in which one additional carbon atom is optionally replaced by a heteroatom selected from O or S in the case of a 5-membered ring, and in which from 1 to 2 additional carbon atoms are optionally replaced by a nitrogen heteroatom, and where the phenyl and heteroaryl are optionally mono-substituted by R$^q$, as defined above; M$^b$ is as defined above; and R$^y$ and R$^z$ are as defined above;

ac) C$_5$-C$_7$ cycloakyl group in which one of the carbon atoms in the ring is replaced by a heteroatom selected from O, S, NH or N(C$_1$-C$_4$ alkyl) and in which one additional carbon atom may be replaced by NH or N(C$_1$-C$_4$ alkyl), and in which at least one carbon atom adjacent to each nitrogen heteroatom has both of its attached hydrogen atoms replaced by one oxygen thus forming a carbonyl moiety and there are one or two carbonyl moieties present in the ring;

ad) C$_2$-C$_4$ alkenyl radical, optionally mono-substituted by one of the substituents a) to ac) above and phenyl which is optionally substituted by R$^q$ as defined above;

ae) C$_2$-C$_4$ alkynyl radical, optionally mono-substituted by one of the substituents a) to ac) above;

af) C$_1$-C$_4$ alkyl radical;

ag) C$_1$-C$_4$ alkyl mono-substituted by one of the substituents a) -ac) above;

ah) a 2-oxazolidinonyl moiety in which the point of attachment is the nitrogen atom of the oxazolidinone ring, the ring oxygen atom is optionally replaced by a heteroatom selected from —S— and NR$^f$ (where R$^f$ is as defined above) and one of the saturated carbons atoms of the oxazolidinone ring is optionally mono-substituted by one of the substituents a) to ag) above; and M is a removable carboxy protecting group.

2. A compound of claim 1 wherein M is selected from the group consisting of alkyl, substituted alkyl, benzyl, substituted benzyl, aryl, substituted aryl, allyl, substituted allyl, and triorganosilyl.

3. A compound of claim 1 wherein M is selected from the group consisting of benzhydryl, p-nitrobenzyl, 2-naphthylmethyl, allyl, 2-chloroallyl, benzyl, 2,2,2-trichloroethyl, t-butyldimethylsilyl, t-butyldiphenylsilyl, trimethylsilyl, 2-(trimethyl)silylethyl, phenacyl, p-methoxybenzyl, acetonyl, o-nitrobenzyl, and 4-pyridylmethyl.

4. A compound of claim 1 wherein P' is selected from the group consisting of trialkylsilyl, aryl(alkyl)alkoxysilyl, alkoxydiarylsilyl, diarylalkylsilyl, alkyloxycarbonyl, substituted alkyloxycarbonyl, benzyloxycarbonyl, substituted benzyloxycarbonyl, allyloxycarbonyl, and substituted allyloxycarbonyl.

5. A compound of claim 1 wherein P' is selected from the group consisting of t-butylmethoxyphenylsilyl, t-butoxydiphenylsilyl, trimethylsilyl, triethylsilyl, t-butyldimethylsilyl, o-nitrobenzyloxycarbonyl, p-nitrobenzyloxycarbonyl, benzyloxycarbonyl, t-butyloxycarbonyl, 2,2,2-trichloroethyloxycarbonyl, and allyloxycarbonyl.

6. A compound of claim 1 of the formula:

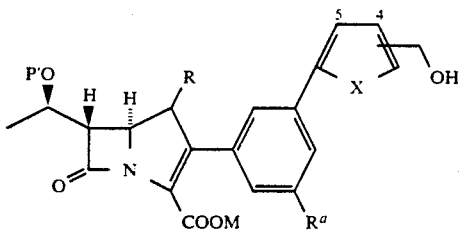

wherein:

R is H or CH$_3$;

P' is a removable protecting group for hydroxy;

M is a removable protecting group for carboxy;

R$^a$ is selected from the group consisting of H, OP', Cl, Br, I, SCH$_3$, CN, CHO, SOCH$_3$, SO$_2$CH$_3$, CO$_2$M, CH$_2$OP' or CONH$_2$; and with the proviso that the —CH$_2$OH substituent is in the 3- or 4-position of the heteroaromatic ring; and X is O or S.

7. A compound of claim 6 wherein M is selected from the group consisting of alkyl, substituted alkyl, benzyl, substituted benzyl, aryl, substituted aryl, allyl, substituted allyl, and triorganosilyl.

8. A compound of claim 6 wherein M is selected from the group consisting of benzhydryl, p-nitrobenzyl, 2-naphthylmethyl, allyl, 2-chloroallyl, benzyl, 2,2,2-trichloroethyl, t-butyldimethylsilyl, tibutyldiphenylsilyl, trimethylsilyl, 2-(trimethyl)silylethyl, phenacyl, p-methoxybenzyl, acteonyl, o-nitrobenzyl, and 4-pyridylmethyl.

9. A compound of claim 6 wherein P' is selected from the group consisting of trialkylsilyl, aryl(alkyl)alkoxysilyl, alkoxydiarylsilyl, diarylalkylsilyl, alkyloxycarbonyl, substituted alkyloxycarbonyl, benzyloxycarbonyl, substituted benxyloxycarbonyl, allyloxycarbonyl, and substituted allyloxycarbonyl.

10. A compound of claim 6 wherein P' is selected from the group consisting of t-butylmethoxy-phenylsilyl, t-butoxydiphenylsilyl, trimethylsilyl, triethylsilyl, t-butyldimethylsilyl, o-nitrobenzyloxycarbonyl, p-nitrobenzyloxycarbonyl, benzyloxycarbonyl, t-butyloxycarbonyl, 2,2,2-trichloroethyloxycarbonyl, and allyloxycarbonyl.

* * * * *